(12) United States Patent
van Duzer et al.

(10) Patent No.: US 9,562,013 B2
(45) Date of Patent: *Feb. 7, 2017

(54) SELECTIVE HDAC3 INHIBITORS

(71) Applicant: Acetylon Pharmaceuticals, Inc., Boston, MA (US)

(72) Inventors: John H. van Duzer, Georgetown, MA (US); Ralph Mazitschek, Belmont, MA (US)

(73) Assignee: Acetylon Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/753,913

(22) Filed: Jun. 29, 2015

(65) Prior Publication Data

US 2015/0299130 A1 Oct. 22, 2015

Related U.S. Application Data

(62) Division of application No. 14/169,732, filed on Jan. 31, 2014, now Pat. No. 9,096,549.

(60) Provisional application No. 61/923,023, filed on Jan. 2, 2014, provisional application No. 61/759,732, filed on Feb. 1, 2013.

(51) Int. Cl.
| | |
|---|---|
| *A61K 31/497* | (2006.01) |
| *A61K 31/495* | (2006.01) |
| *A61K 31/5377* | (2006.01) |
| *A61K 31/415* | (2006.01) |
| *C07D 215/54* | (2006.01) |
| *C07D 241/44* | (2006.01) |
| *C07D 217/26* | (2006.01) |
| *C07D 215/38* | (2006.01) |
| *C07D 235/06* | (2006.01) |
| *C07D 471/04* | (2006.01) |
| *C07D 209/34* | (2006.01) |
| *C07D 231/56* | (2006.01) |
| *C07D 235/08* | (2006.01) |

(52) U.S. Cl.
CPC .......... *C07D 215/54* (2013.01); *A61K 31/415* (2013.01); *A61K 31/495* (2013.01); *A61K 31/497* (2013.01); *A61K 31/5377* (2013.01); *C07D 209/34* (2013.01); *C07D 215/38* (2013.01); *C07D 217/26* (2013.01); *C07D 231/56* (2013.01); *C07D 235/06* (2013.01); *C07D 235/08* (2013.01); *C07D 241/44* (2013.01); *C07D 471/04* (2013.01)

(58) Field of Classification Search
USPC ... 514/234.5, 253.06, 418, 394, 249, 253.05
See application file for complete search history.

(56) References Cited

U.S. PATENT DOCUMENTS

| | | |
|---|---|---|
| 6,897,220 B2 | 5/2005 | Delmore et al. |
| 7,595,343 B2 | 9/2009 | Delmore et al. |
| 7,838,520 B2 | 11/2010 | Delmore et al. |
| 7,868,204 B2 | 1/2011 | Delmore et al. |
| 9,096,549 B2 | 8/2015 | van Duzer |
| 9,139,583 B2 | 9/2015 | van Duzer |
| 2014/0249148 A1* | 9/2014 | van Duzer et al. ........ 514/234.5 |

FOREIGN PATENT DOCUMENTS

| | | |
|---|---|---|
| CN | 102050791 A | 5/2011 |
| WO | 03013484 A2 | 2/2003 |
| WO | 03024448 A2 | 3/2003 |
| WO | 2005/092899 A1 | 10/2005 |
| WO | 2006/115845 A1 | 11/2006 |
| WO | 2007/087129 A2 | 8/2007 |
| WO | 2009037001 A2 | 3/2009 |
| WO | 2010102811 A1 | 9/2010 |
| WO | 2011109059 A1 | 9/2011 |
| WO | 2012149540 A1 | 11/2012 |

OTHER PUBLICATIONS

Cancer [online], [retrieved on Jul. 6, 2007] Retrieved from the Internet, URL: http://www.nlm.nih.gov/medlineplus/cancer.html.*

Lala et al., Role of nitric oxide in tumor progression: Lessons from experimental tumors, Cancer and Metastasis Reviews (1998), 17, 91-106.*

Golub et al., Molecular Classification of Cancer: Class Discovery and Class Prediction by Gene Expression Monitoring, Science (1999), vol. 286, 531-537.*

Beglopoulos et al. (2006) "Regulation of CRE-dependent transcription by presenilins: prospects for therapy of Alzheimer's disease," Trends in Pharmacological Sciences. 27(1):33-40.

Fakih et al. (May 12, 2010) "A Phase I, Pharmacokinetic, and Pharmacodynamic Study of Two Schedules of Vorinostat in Combination with 5-Fluorouracil and Leucovorin in Patients with Refractory Solid Tumors," Clinical Cancer Research. 16(14):3786-3794.

Fischer et al. (2007) "Recovery of learning and memory is associated with chromatin remodelling," Nature. 447:178-182.

Galmozzi (Mar. 2013) "Inhibition of Class I Histone Deacetylases Unveils a Mitochondrial Signature and Enhances Oxidative Metabolism in Skeletal Muscle and Adipose Tissue," Diabetes. 62:732-742.

Kozikowski et al. (2007) "Functional Differences in Epigenetic ModulatorsSuperiority of Mercaptoacetamide-Based Histone Deacetylase Inhibitors Relative to Hydroxamates in Cortical Neuron Neuroprotection Studies," J. Med. Chem. 50:3054-3061.

(Continued)

*Primary Examiner* — Samantha Shterengarts
(74) *Attorney, Agent, or Firm* — Lathrop & Gage LLP; Brian C. Trinque

(57) ABSTRACT

Provided herein are HDAC3 inhibitors, as well as methods of treatment comprising administering these compounds to a subject in need thereof.

11 Claims, No Drawings

(56) References Cited

OTHER PUBLICATIONS

Lundh et al. (Jul. 7, 2012) "Histone deacetylases 1 and 3 but not 2 mediate cytokine-induced beta cell apoptosis in INS-1 cells and dispersed primary islets from rats and are differentially regulated in the islets of type 1 diabetic children," Diabetologia. 55:2421-2431.
McQuown et al. (Jan. 12, 2011) "HDAC3 Is a Critical Negative Regulator of Long-Term Memory Formation," The Journal of Neuroscience. 31(2):764-774.
Mihaylova et al. (May 13, 2011) "Class IIa Histone Deacetylases Are Hormone-Activated Regulators of FOXO and Mammalian Glucose Homeostasis," Cell. 145:607-621.
Spurling et al. (2008) "HDAC3 overexpression and colon cancer cell proliferation and differentiation," Molecular Carcinogenesis. 47:137-147.
Witt et al. (2009) "HDAC family: What are the cancer relevant targets?" Cancer Letters. 277:8-21.
International Search Report with Written Opinion corresponding to International Patent Application No. PCT/US2014/014128, mailed Mar. 19, 2014.
Extended European Search Report corresponding to European Patent Application No. 14745382.3, dated May 23, 2016.

* cited by examiner

SELECTIVE HDAC3 INHIBITORS

PRIORITY BENEFIT

This application is a divisional of U.S. application Ser. No. 14/169,732, filed Jan. 31, 2014, which claims the benefit U.S. Provisional Application Ser. No. 61/759,732, filed Feb. 1, 2013, and U.S. Provisional Application Ser. No. 61/923,023, filed Jan. 2, 2014,the contents of which are incorporated herein in their entirety.

BACKGROUND OF THE INVENTION

A biological target of recent interest is histone deacetylase (HDAC) (see, for example, a discussion of the use of inhibitors of histone deacetylases for the treatment of cancer: Marks et al. *Nature Reviews Cancer* 2001, 7,194; Johnstone et al. *Nature Reviews Drug Discovery* 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown effective in treating an otherwise recalcitrant cancer (Warrell et al. *J. Natl. Cancer Inst.* 1998, 90, 1621-1625).

At this time, eleven human HDACs, which use Zn as a cofactor, have been identified (Taunton et al. *Science* 1996, 272, 408-411; Yang et al. *J. Biol. Chem.* 1997, 272, 28001-28007; Grozinger et al. *Proc. Natl. Acad. Sci.* U.S.A. 1999, 96, 4868-4873; Kao et al. Genes Dev. 2000, 14, 55-66; Hu et al. *J. Biol. Chem.* 2000, 275, 15254-15264; Zhou et al. *Proc. Natl. Acad. Sci U.S.A.* 2001, 98, 10572-10577; Venter et al. *Science* 2001, 291, 1304-1351) and these members fall into three classes (class I, II, and IV) based on sequence homology to their yeast orthologues (O. Witt et al. *Cancer Letters*, 2009, 277, 8-21). Class I HDACs include HDAC1, HDAC2, HDAC3, and HDAC8, and are referred to as "classical" HDACs which implies a catalytic pocket with a $Zn^{2+}$ ion at its base.

There remains a need for preparing structurally diverse HDAC inhibitors, particularly ones that are potent and/or selective inhibitors of particular classes of HDACs and individual HDACs.

SUMMARY OF THE INVENTION

Provided herein are compounds, pharmaceutical compositions comprising such compounds, and methods of using such compounds and compositions to treat or prevent diseases or disorders associated with HDAC activity, particularly diseases or disorders that involve any form of HDAC3 expression. Such diseases include hemoglobinopathy, sickle cell disease (SCD), thalassemia, hematologic malignancies, solid tumors and neurodegenerative diseases.

Thus, in one aspect, provided herein is a compound of Formula I:

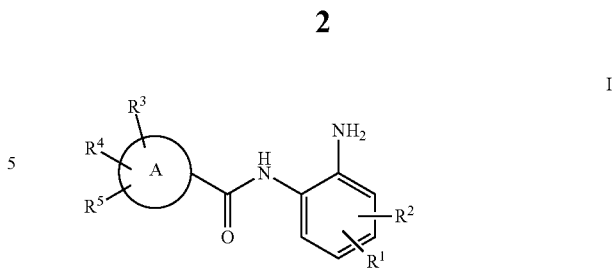

or a pharmaceutically acceptable salt thereof.

In another aspect, provided herein is a compound of Formula II:

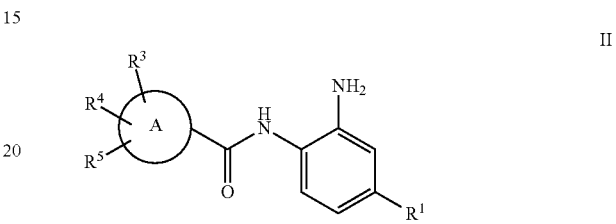

or a pharmaceutically acceptable salt thereof.

In yet another aspect, provided herein is a compound of Formula III:

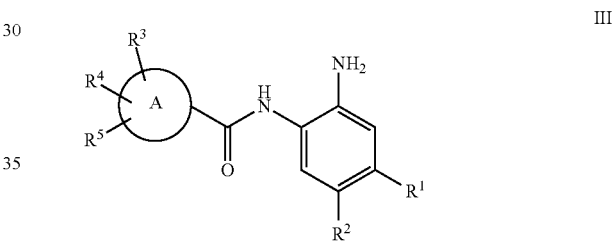

or a pharmaceutically acceptable salt thereof.

In another aspect, provided herein is a compound of Formula IV:

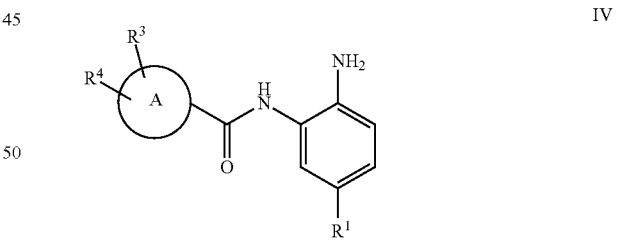

or a pharmaceutically acceptable salt thereof.

In another aspect, provided herein is a pharmaceutical composition comprising any of the compounds of the instant invention (Formula I, II, III, IV, or any of the compounds presented in Table 1) or a pharmaceutically acceptable salt thereof, together with a pharmaceutically acceptable carrier.

In another aspect, provided herein is a method of inhibiting HDAC3 in a subject, comprising administering a compound of Formula I, II, III, IV, or any of the compounds presented in Table 1, or a pharmaceutically acceptable salt thereof.

In another aspect, provided herein is a method of selectively inhibiting HDAC3 over other HDACs in a subject, comprising administering a compound of Formula I, II, III, IV, or any of the compounds presented in Table 1, or a pharmaceutically acceptable salt thereof. In one embodiment, the compound has a selectivity of 5 to 1000 fold for HDAC3. In another embodiment, the compound has a selectivity for HDAC3 when tested in a HDAC enzyme assay of about 5 to 1000 fold.

In another aspect, provided herein is a method of treating a disease mediated by HDAC3 in a subject comprising administering to the subject a compound of Formula I, II, III, IV, or any of the compounds presented in Table 1, or a pharmaceutical composition thereof.

In yet another aspect, provided herein is a method of treating a disease in a subject comprising administering to the subject a compound of Formula I, II, III, IV, or any of the compounds presented in Table 1, or a pharmaceutical composition thereof.

In one embodiment, provided herein is a method of treating hemoglobinopathy in a subject comprising administering to the subject a compound of Formula I, II, III, IV, or any of the compounds presented in Table 1, or a pharmaceutical composition thereof. In another embodiment, provided herein is a method of treating sickle cell disease (SCD) in a subject comprising administering to the subject a compound of Formula I, II, III, IV, or any of the compounds presented in Table 1, or a pharmaceutical composition thereof. In another embodiment, provided herein is a method of treating thalassemia in a subject comprising administering to the subject a compound of Formula I, II, III, IV, or any of the compounds presented in Table 1, or a pharmaceutical composition thereof.

In certain embodiments, provided herein is a method of treating a cancer or a proliferation disease in a subject comprising administering to the subject a compound of Formula I, II, III, IV, or any of the compounds presented in Table 1, or a pharmaceutical composition thereof. In one embodiment, the cancer is a hematologic malignancy. The hematologic malignancy can be leukemia or lymphoma. The leukemia can further be acute lymphoblastic leukemia (ALL), acute myelogenous leukemia (AML), chronic lymphocytic leukemia (CLL), chronic myelogenous leukemia (CML), acute monocytic leukemia (AML), or acute promyelocytic leukemia (APL). The lymphoma can be Hodgkin's lymphoma or Non-Hodgkin's lymphoma. In yet another embodiment, the cancer is a solid tumor. The solid tumor can be a brain tumor, neuroblastoma, retinoblastoma, Wilm's tumor, bone tumors, soft-tissue sarcomas, head cancer, neck cancer, gastric cancer, prostate cancer, bladder cancer, renal cancer, cancer of the uterus, ovarian cancer, testicular cancer, colon cancer, lung cancer, or breast cancer. The solid tumor can also be gastric cancer, prostate cancer, or colon cancer.

In other embodiments, provided herein is a method of treating a neurodegenerative disease in a subject comprising administering to the subject a compound of Formula I, II, III, IV, or any of the compounds presented in Table 1, or a pharmaceutical composition thereof. The neurodegenerative disease can be Huntington's disease, Friedrich's ataxia, myotonic dystrophy, Parkinson's disease, spinocerebellar ataxia, Kennedy's disease, amyotrophic lateral sclerosis, spinal and bulbar muscular atrophy, or Alzheimer's disease.

In certain embodiment, provided herein is a method of treating a disease which causes memory deficits comprising administering to the subject a compound of Formula I, II, III, IV, or any of the compounds presented in Table 1, or a pharmaceutical composition thereof.

In other embodiments, provided herein is a method of treating metabolic disease in a subject comprising administering to the subject a compound of Formula I, II, III, IV, or any of the compounds presented in Table 1, or a pharmaceutical composition thereof. The metabolic disease can be type 2 diabetes.

In a further embodiment of the methods of treatment described herein, the subject is a human.

DETAILED DESCRIPTION OF THE INVENTION

HDAC inhibitors are capable of de-repressing γ-globin gene expression and inducing production of HbF ($\alpha_2\gamma_2$). Clinical severity of hemoglobinopathy and thalassemia can be reduced by enhancing expression of fetal hemoglobin (γ-globin), producing HbF ($\alpha_2\gamma_2$) (Boosalis et al., *Blood Cells, Molecules, and Diseases* 2011, 15, 107). Sickle cell disease (SCD) is also demonstrated to be treated by induction of fetal hemoglobin (HbF) (Mabaera et al., *Experimental Hematology* 2008, 1057). Therefore, HDAC inhibitors are promising molecules for treatment of hemoglobinopathy, thalassemia and SCD.

In addition, HDACs play an important role in cell proliferation and differentiation. HDAC inhibition has been demonstrated modulating the balance between pro- and anti-apoptotic proteins, upregulating the intrinsic and extrinsic apoptosis pathway, and leading to cell cycle arrest. Thus, HDACs are a compelling therapeutic target for cancer therapy. Some HDAC inhibitors have been shown to induce differentiation and cell death in myeloid and lymphoid model systems (Melnick et al., *Current Opinion in Hematology* 2002, 9, 322). In particular, HDAC3 is identified as a key component of the aberrant transcription regulation in acute promyelocytic leukemia cells (Witt et al., *Cancer Letters* 2009, 277, 8). Therefore, HDAC inhibitors, and HDAC3 inhibitors in particular, can provide benefit to treatment of hematologic malignancies.

HDAC3 is also found to be significantly associated with poor prognosis in a large series of gastric, prostate and colorectal cancers (Witt et al., *Cancer Letters* 2009, 277, 8). Another study of a variety of human cancers indicates that HDAC3 may be one of the most frequently upregulated genes in cancer cells (Spurling et al., *Molecular Carcinogenesis* 2008, 47, 137). Together with HDAC1 and HDAC2, HDAC3 is found overexpressed in colonic tumors and thus may be an important target for cancer therapy (Fakih et al., *Clinical Cancer Research* 2010, 16, 3786). In addition, cell lines from other cancers, such as breast cancer, hepatic cancer and neuronal cancer, are found to be induced to differentiate by HDAC inhibitors.

Furthermore, HDAC inhibitors have been found to be protective in different cellular and animal models of acute and chronic neurodegenerative diseases, such as Huntington's disease, as well as spinal and bulbar muscular atrophy (Kozikowski et al., *J. Med. Chem.* 2007, 50, 3054). Some studies suggest that HDAC inhibitors can reduce memory deficits and neurodegeneration in animal models of Alzheimer disease and improve learning behavior (Begloupoulos et al., *Trends in Pharmacological Sciences* 2006, 27, 33; Fischer et al., *Nature* 2007, 447, 178). A recent study found that selective inhibition of HDAC3 significantly enhanced long-term memory in a persistent manner (McQuown et al., *J Neurosci* 2011, 31, 764). However, the mechanism of the reported improvement of neurodegenerative diseases and long-term memory formation by HDAC inhibitors is not fully understood. Thus, inhibition of HDAC3 with the compounds disclosed herein can be advantageous in the treatment of neurodegenerative diseases and the improvement of long-term memory formation.

Class I HDAC inhibitors have also been demonstrated to reduce body weight and glucose and insulin levels in obese diabetic mice (Galmozzi et al., Diabetes 2012). Thus, class I HDAC inhibitors have been suggested to be potential therapeutics for type 2 diabetes (Mihaylova et al., *Cell* 2011, 145, 607; Galmozzi et al., Diabetes 2012). Targeting HDAC1 and HDAC3 is found to be able to provide optimal protection of beta cell mass and function in clinical islet transplantation and recent-onset type 1 diabetic patients (Lundh et al., *Diabetologia* 2012, 55, 2421).

Accordingly, provided herein are compounds, pharmaceutical compositions comprising such compounds, and methods of using such compounds and compositions to treat or prevent diseases or disorders associated with HDAC activity. The compounds are, in particular, able to inhibit HDAC3 activity.

Definitions

Listed below are definitions of various terms used to describe this invention. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkyl," as used herein, refers to saturated, straight- or branched-chain hydrocarbon moieties containing, in certain embodiments, between one and six, or one and eight carbon atoms, respectively. Examples of $C_{1-6}$ alkyl moieties include, but are not limited to, methyl, ethyl, propyl, isopropyl, n-butyl, tert-butyl, neopentyl, n-hexyl moieties; and examples of $C_{1-8}$ alkyl moieties include, but are not limited to, methyl, ethyl, propyl, isopropyl, n-butyl, tert-butyl, neopentyl, n-hexyl, heptyl, and octyl moieties.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have 6 carbon atoms. In some embodiments, aryl groups have from six to ten carbon atoms. In some embodiments, aryl groups have from six to sixteen carbon atoms.

The term "cycloalkyl," as used herein, denotes a monovalent group derived from a monocyclic or polycyclic saturated or partially unsatured carbocyclic ring compound. Examples of $C_{3-8}$-cycloalkyl include, but not limited to, cyclopropyl, cyclobutyl, cyclopentyl, cyclohexyl, cycloheptyl and cyclooctyl; and examples of $C_{3-12}$-cycloalkyl include, but not limited to, cyclopropyl, cyclobutyl, cyclopentyl, cyclohexyl, bicyclo[2.2.1]heptyl, and bicyclo[2.2.2]octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, moieties or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolylm thiadiazolyl, oxazolyl, oxadiazolyl, thiophenyl, furanyl, quinolinyl, isoquinolinyl, benzimidazolyl, benzooxazolyl, quinoxalinyl, acridinyl, and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

In accordance with the invention, any of the aryls, substituted aryls, heteroaryls and substituted heteroaryls described herein, can be any aromatic group.

The terms "halo" and "halogen," as used herein, refer to an atom selected from fluorine, chlorine, bromine and iodine.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted" and any other optionally substituted group as used herein, refer to groups that are substituted or unsubstituted by independent replacement of one, two, or three or more of the hydrogen atoms thereon with substituents including, but not limited to:

alkyl, alkenyl, alkynyl, cycloalkyl, aryl, heterocycloalkyl, heteroaryl,

—F, —Cl, —Br, —I,
—OH,
—$NO_2$, —CN,
—$NH_2$, —NH—$C_1$-$C_{12}$-alkyl, —NH-aryl, -dialkylamino,
—O—$C_1$-$C_{12}$-alkyl, —O-aryl,
—C(O)—, —C(O)O—, —C(O)NH—, —OC(O)—, —OC(O)O—, —OC(O)NH—, —NHC(O)—, —NHC(O)O—,
—C(O)—$C_1$-$C_{12}$-alkyl, —C(O)—$C_3$-$C_{12}$-cycloalkyl, —C(O)-aryl, —C(O)-heteroaryl, —C(O)—heterocycloalkyl,
—C(O)O—$C_1$-$C_{12}$-alkyl, —C(O)O—$C_3$-$C_{12}$-cycloalkyl, —C(O)O-aryl, —C(O)O-heteroaryl, —C(O)O-heterocycloalkyl,
—$CONH_2$, —CONH—$C_1$-$C_{12}$-alkyl, —CONH-aryl, —$OCO_2$—$C_1$-$C_{12}$-alkyl, —$OCO_2$-aryl, —$OCONH_2$, —OCONH—$C_1$-$C_{12}$-alkyl, —OCONH-aryl,
—NHC(O)—$C_1$-$C_{12}$-alkyl, —NHC(O)-aryl, —$NHCO_2$—$C_1$-$C_{12}$-alkyl, —$NHCO_2$-aryl,
—S(O)—$C_1$-$C_{12}$-alkyl, —S(O)-aryl, —$SO_2$NH—$C_1$-$C_{12}$-alkyl, —$SO_2$NH-aryl,
—$NHSO_2$—$C_1$-$C_{12}$-alkyl, —$NHSO_2$-aryl,
—SH, —S—$C_1$-$C_{12}$-alkyl, or —S-aryl.

In certain embodiments, the optionally substituted groups include the following: $C_1$-$C_{12}$-alkyl, $C_2$-$C_{12}$-alkenyl, $C_2$-$C_{12}$-alkynyl, $C_3$-$C_{12}$-cycloalkyl, $C_3$-$C_{12}$-aryl, $C_3$-$C_{12}$-heterocycloalkyl, or $C_3$-$C_{12}$-heteroaryl.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "inhibitor" is synonymous with the term antagonist.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating" and "treatment" refer to a method of alleviating or abating a disease and/or its attendant symptoms.

The term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

Compounds of the Invention

In one aspect, the invention provides a compound of Formula I:

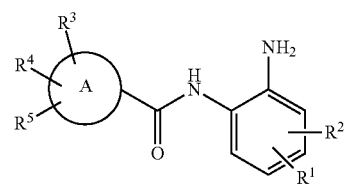

or a pharmaceutically acceptable salt thereof,
wherein
A is bicyclic heteroaryl or bicyclic heterocycloalkyl;
$R^1$ and $R^2$ are each independently selected from H or halo;
$R^3$ is H, heterocycloalkyl, or $C_{1-6}$-alkyl-heterocycloalkyl wherein the heterocycloalkyl or $C_{1-6}$-alkyl-heterocycloalkyl groups are optionally substituted;
$R^4$ and $R^5$ are each independently selected from H, $C_{1-6}$-alkyl, $C_{2-6}$-alkenyl, $C_{2-6}$-alkynyl, $C_{3-6}$-cycloalkyl, $C_{1-6}$- alkyl-$C_{3-6}$-cycloalkyl, heterocycloalkyl, $C_{1-6}$-alkyl-heterocycloalkyl, $NR^6R^7$, O—$C_{1-6}$-alkyl-$OR^8$, $C_{1-6}$-alkyl-$OR^8$, aryl, $C_{1-6}$-alkyl-aryl, heteroaryl, $C_{1-6}$-alkyl-heteroaryl, C(O)N($R^6$)-heteroaryl, C(O)N($R^6$)-heterocycloalkyl, C(O)N($R^6$)-aryl, C(O)—$NR^6R^7$, C(O)-heteroaryl, C(O)-heterocycloalkyl, C(O)-aryl, C(O)—$C_{1-6}$-alkyl, $CO_2$-heteroaryl, $CO_2$-heterocycloalkyl, $CO_2$-aryl, $CO_2$—$C_{1-6}$-alkyl, or C(O)—$C_{1-6}$-alkyl-heterocycloalkyl, wherein the cycloalkyl, heterocycloalkyl, aryl, or heteroaryl groups are optionally substituted;

$R^6$ and $R^7$ are each independently selected from H, $C_{1-6}$-alkyl, $C_{1-6}$-alkyl-$OR^8$, $CO_2R^8$, or $C_1$-$C_6$-alkyl-aryl; and $R^8$ is H or $C_{1-6}$-alkyl.

In one embodiment of the compound of Formula I, the heterocycloalkyl or $C_{1-6}$-alkyl-heterocycloalkyl groups are optionally substituted with $C_{1-4}$-alkyl;

and the cycloalkyl, heterocycloalkyl, aryl, or heteroaryl groups of $R^4$ and $R^5$ are optionally substituted with $C_{1-4}$-alkyl, $CO_2R^8$, $C(O)R^8$, or $C_{1-6}$-alkyl-$OR^8$.

In an embodiment of the compound of Formula I, A is a bicyclic heteroaryl or bicyclic heterocycloalkyl selected from the group consisting of

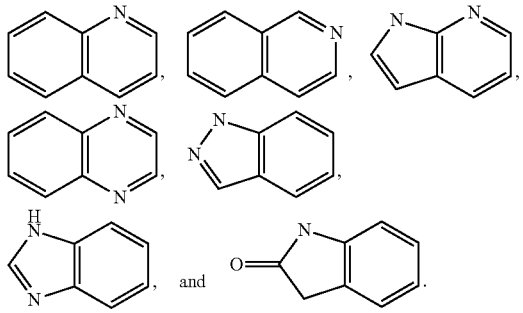

In another embodiment of the compound of Formula I, A is a bicyclic heteroaryl or bicyclic heterocycloalkyl selected from the group consisting of

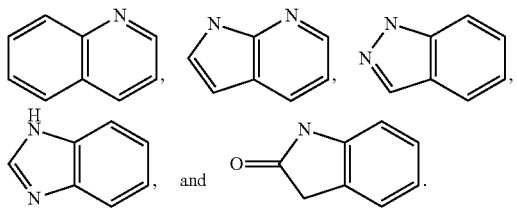

In one embodiment of the compound of Formula I, $R^1$ is halo. $R^1$ can be fluoro.

In a further embodiment of the compound of Formula I, $R^1$ is para to the $NH_2$ or para to the amide bond (NHC(O)—).

In another embodiment of the compound of Formula I, $R^2$ is halo. $R^2$ can be chloro.

In another embodiment of the compound of Formula I, $R^1$ is fluoro and $R^2$ is H.

In another embodiment of the compound of Formula I, $R^3$ is heterocycloalkyl, or $C_{1-6}$-alkyl-heterocycloalkyl, and the heterocycloalkyl or $C_{1-6}$-alkyl-heterocycloalkyl groups can be optionally substituted with $C_{1-4}$-alkyl. $R^3$ can be piperazinyl or piperazinyl-$CH_3$. $R^3$ can also be $CH_2CH_2$-morpholinyl.

In another embodiment of the compound of Formula I, $R^4$ is independently selected from H, $C_{3-6}$-cycloalkyl, $C_{1-6}$-alkyl-$C_{3-6}$-cycloalkyl, heterocycloalkyl, or $C_{1-6}$-alkyl-heterocycloalkyl. $R^4$ can also be independently selected from H or $C_{3-6}$-cycloalkyl. $R^4$ can be H only. $R^4$ can also be $C_{3-6}$-cycloalkyl only.

In yet another embodiment of the compound of Formula I, $R^5$ is H.

In a preferred embodiment of the compound of Formula I, $R^3$ is heterocycloalkyl, or $C_{1-6}$-alkyl-heterocycloalkyl, and $R^4$ and $R^5$ are both H. In another preferred embodiment of the compound of Formula I, $R^3$ is heterocycloalkyl, or $C_{1-6}$-alkyl-heterocycloalkyl, wherein the heterocycloalkyl or $C_{1-6}$-alkyl-heterocycloalkyl groups can be optionally substituted with $C_{1-4}$-alkyl, $R^4$ is $C_{3-6}$-cycloalkyl, and $R^5$ is H.

In another aspect, the invention provides a compound of Formula II:

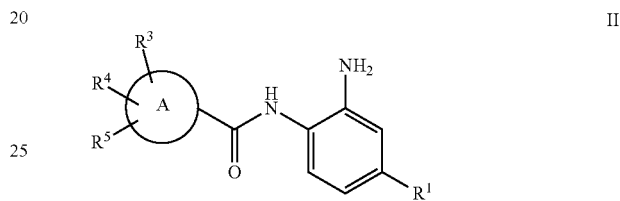

or a pharmaceutically acceptable salt thereof,
wherein
A is bicyclic heteroaryl or bicyclic heterocycloalkyl;
$R^1$ is selected from H or halo;
$R^3$ is H, heterocycloalkyl, or $C_{1-6}$-alkyl-heterocycloalkyl wherein the heterocycloalkyl or $C_{1-6}$-alkyl-heterocycloalkyl groups are optionally substituted;
$R^4$ and $R^5$ are each independently selected from H, $C_{1-6}$-alkyl, $C_{2-6}$-alkenyl, $C_{2-6}$-alkynyl, $C_{3-6}$-cycloalkyl, $C_{1-6}$-alkyl-$C_{3-6}$-cycloalkyl, heterocycloalkyl, $C_{1-6}$-alkyl-heterocycloalkyl, $NR^6R^7$, O—$C_{1-6}$-alkyl-$OR^8$, $C_{1-6}$-alkyl-$OR^8$, aryl, $C_{1-6}$-alkyl-aryl, heteroaryl, $C_{1-6}$-alkyl-heteroaryl, C(O)N($R^6$)-heteroaryl, C(O)N($R^6$)-heterocycloalkyl, C(O)N($R^6$)-aryl, C(O)—$NR^6R^7$, C(O)-heteroaryl, C(O)-heterocycloalkyl, C(O)-aryl, C(O)—$C_{1-6}$-alkyl, $CO_2$-heteroaryl, $CO_2$-heterocycloalkyl, $CO_2$-aryl, $CO_2$—$C_{1-6}$-alkyl, or C(O)—$C_{1-6}$-alkyl-heterocycloalkyl, wherein the cycloalkyl, heterocycloalkyl, aryl, or heteroaryl groups are optionally substituted;

$R^6$ and $R^7$ are each independently selected from H, $C_{1-6}$-alkyl, $C_{1-6}$-alkyl-$OR^8$, $CO_2R^8$, or $C_1$-$C_6$-alkyl-aryl; and $R^8$ is H or $C_{1-6}$-alkyl.

In one embodiment of the compound of Formula II, $R^1$ is fluoro.

In another embodiment of the compound of Formula II, $R^3$ heterocycloalkyl, or $C_{1-6}$-alkyl-heterocycloalkyl, and the heterocycloalkyl or $C_{1-6}$-alkyl-heterocycloalkyl groups can be optionally substituted. $R^3$ can be piperazinyl or piperazinyl-$CH_3$. $R^3$ can also be $CH_2CH_2$-morpholinyl.

In another embodiment of the compound of Formula II, $R^4$ is independently selected from H, $C_{3-6}$-cycloalkyl, $C_{1-6}$-alkyl-$C_{3-6}$-cycloalkyl, heterocycloalkyl, or $C_{1-6}$-alkyl-heterocycloalkyl. $R^4$ can also be independently selected from H or $C_{3-6}$-cycloalkyl. $R^4$ can be H only. $R^4$ can also be $C_{3-6}$-cycloalkyl only.

In yet another embodiment of the compound of Formula II, $R^5$ is H.

In another aspect, the invention provides a compound of Formula III:

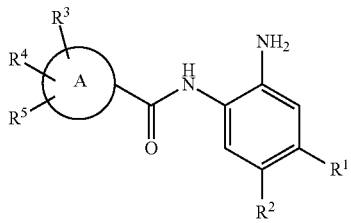

III

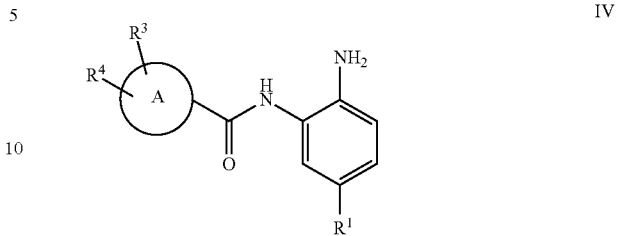

IV or a pharmaceutically acceptable salt thereof,
wherein
A is bicyclic heteroaryl or bicyclic heterocycloalkyl;
$R^1$ and $R^2$ are halo;
$R^3$ is H, heterocycloalkyl, or $C_{1-6}$-alkyl-heterocycloalkyl;
$R^4$ and $R^5$ are each independently selected from H, $C_{1-6}$-alkyl, $C_{2-6}$-alkenyl, $C_{2-6}$-alkynyl, $C_{3-6}$-cycloalkyl, $C_{1-6}$-alkyl-$C_{3-6}$-cycloalkyl, heterocycloalkyl, $C_{1-6}$-alkyl-heterocycloalkyl, $NR^6R^7$, O—$C_{1-6}$-alkyl-$OR^8$, $C_{1-6}$-alkyl-$OR^8$, aryl, $C_{1-6}$-alkyl-aryl, heteroaryl, $C_{1-6}$-alkyl-heteroaryl, C(O)N($R^6$)-heteroaryl, C(O)N($R^6$)-heterocycloalkyl, C(O)N($R^6$)-aryl, C(O)—$NR^6R^7$, C(O)-heteroaryl, C(O)-heterocycloalkyl, C(O)-aryl, C(O)—$C_{1-6}$-alkyl, $CO_2$-heteroaryl, $CO_2$-heterocycloalkyl, $CO_2$-aryl $CO_2$—$C_{1-6}$-alkyl, or C(O)—$C_{1-6}$-alkyl-heterocycloalkyl, wherein the cycloalkyl, heterocycloalkyl, aryl, or heteroaryl groups are optionally substituted;
$R^6$ and $R^7$ are each independently selected from H, $C_{1-6}$-alkyl, $C_{1-6}$-alkyl-$OR^8$, $CO_2R^8$, or $C_1$-$C_6$-alkyl-aryl; and
$R^8$ is H or $C_{1-6}$-alkyl.
In one embodiment of the compound of Formula III, $R^1$ is chloro and $R^2$ is fluoro.
In another embodiment of the compound of Formula III, $R^3$ is H, $R^4$ is H, and $R^5$ is H.

In another aspect, the invention provides a compound of Formula IV:

or a pharmaceutically acceptable salt thereof,
wherein
A is bicyclic heteroaryl or bicyclic heterocycloalkyl;
$R^1$ is H or halo;
$R^3$ is heterocycloalkyl, or $C_{1-6}$-alkyl-heterocycloalkyl;
$R^4$ is selected from $C_{3-6}$-cycloalkyl, $C_{1-6}$-alkyl-$C_{3-6}$-cycloalkyl, heterocycloalkyl, $C_{1-6}$-alkyl-heterocycloalkyl, aryl, $C_{1-6}$-alkyl-aryl, heteroaryl, $C_{1-6}$-alkyl-heteroaryl wherein the cycloalkyl, heterocycloalkyl, aryl, or heteroaryl groups are optionally substituted.
In one embodiment of the compound of Formula IV, $R^1$ is halo. $R^1$ can be fluoro.
In another embodiment of the compound of Formula IV, $R^3$ is heterocycloalkyl. $R^3$ can be piperazinyl.
In another embodiment of the compound of Formula IV, $R^4$ is cycloalkyl.
In yet another embodiment of the compound of Formula IV, $R^4$ is cyclopropyl. In one aspect, provided herein is a compound selected from the group consisting of the following compounds in Table 1 below, or pharmaceutically acceptable salts thereof. The assay conditions used to acquire the HDAC inhibition data are described in Example 18.

TABLE 1

| Compound ID | Structures | IC 50 (nM) | | |
| --- | --- | --- | --- | --- |
| | | HDAC1 | HDAC2 | HDAC3 |
| A | 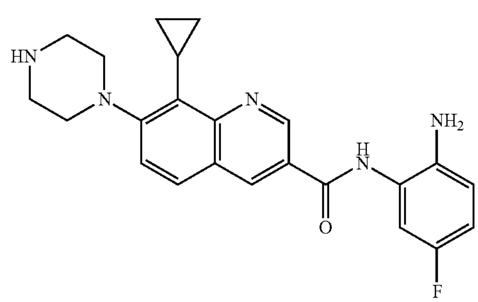 [SMILES: Nc1ccc(F)cc1NC(=O)c1cnc2c(C3CC3)c(N3CCNCC3)ccc2c1] | 468 | 455 | 59 |
| B | 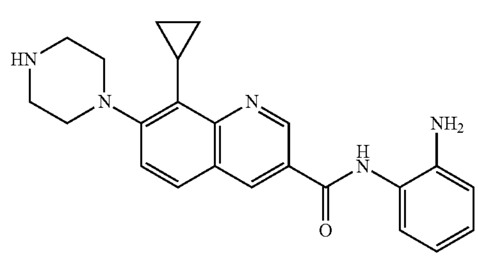 [SMILES: Nc1ccccc1NC(=O)c1cnc2c(C3CC3)c(N3CCNCC3)ccc2c1] | 355 | 372 | 53 |

TABLE 1-continued

| Compound ID | Structures | IC 50 (nM) | | |
|---|---|---|---|---|
| | | HDAC1 | HDAC2 | HDAC3 |
| C | 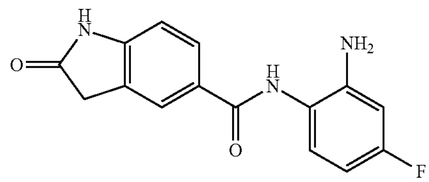 [SMILES: Nc1cc(F)ccc1NC(=O)c1ccc2c(c1)CC(=O)N2] | No inhibition | >2000 | 269 |
| D | 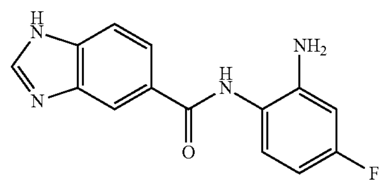 [SMILES: Nc1cc(F)ccc1NC(=O)c1ccc2[nH]cnc2c1] | No inhibition | >2000 | 282 |
| E | 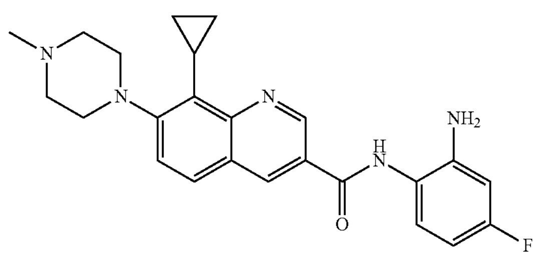 [SMILES: CN1CCN(c2ccc3cc(C(=O)Nc4ccc(F)cc4N)cnc3c2C2CC2)CC1] | 1606 | 805 | 68 |
| F | 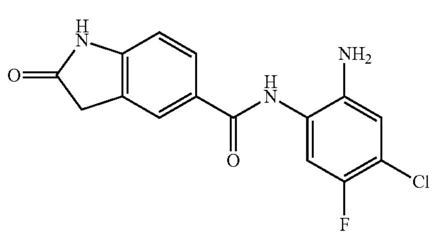 [SMILES: Nc1cc(Cl)c(F)cc1NC(=O)c1ccc2c(c1)CC(=O)N2] | | | |
| G | 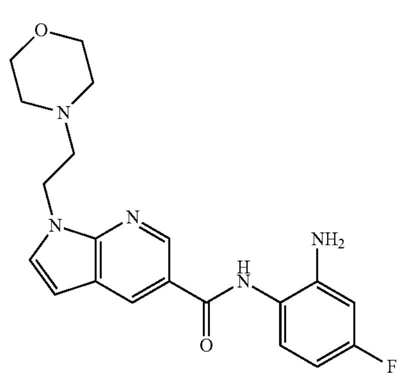 | >2000 | 1532 | 193 |

TABLE 1-continued
| Compound ID | Structures | IC 50 (nM) | | |
|---|---|---|---|---|
| | | HDAC1 | HDAC2 | HDAC3 |
| H | 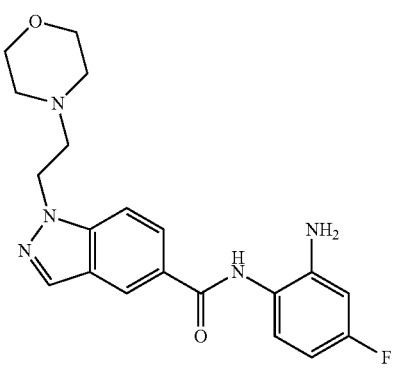 | >2000 | 1780 | 320 |
| I | 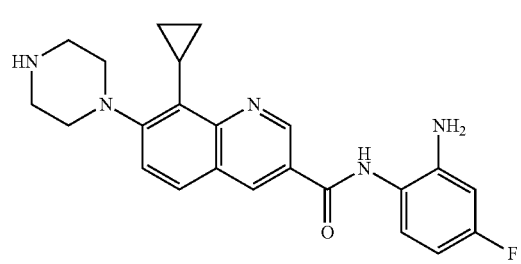 [SMILES: Nc1cc(F)ccc1NC(=O)c1cnc2c(C3CC3)c(N3CCNCC3)ccc2c1] | >2000 | 589 | 57 |
| J | 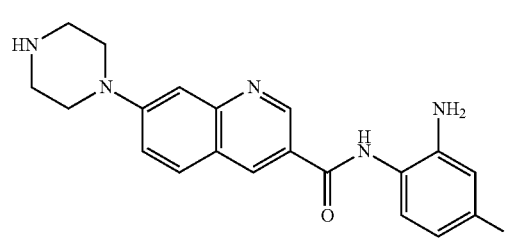 | No inhibition | >2000 | 470 |
| K | 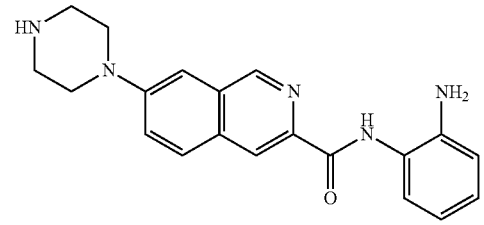 [SMILES: Nc1ccccc1NC(=O)c1cc2ccc(N3CCNCC3)cc2cn1] | 299 | 271 | 38 |
| L | 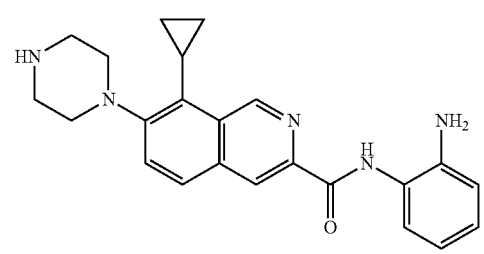 [SMILES: Nc1ccccc1NC(=O)c1cc2ccc(N3CCNCC3)c(C3CC3)c2cn1] | 228 | 212 | 33 |

TABLE 1-continued

| Compound ID | Structures | IC 50 (nM) | | |
|---|---|---|---|---|
| | | HDAC1 | HDAC2 | HDAC3 |
| M | 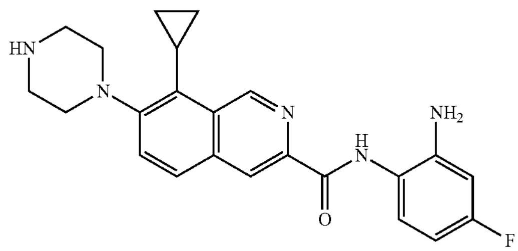 [SMILES: Nc1cc(F)ccc1NC(=O)c1cc2ccc(N3CCNCC3)c(C3CC3)c2cn1] | 462 | 228 | 30 |
| N | 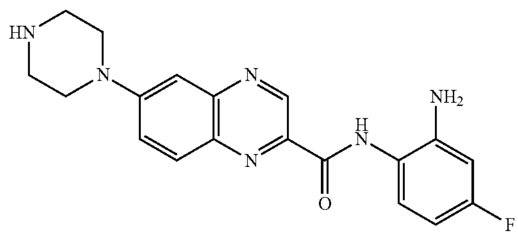 [SMILES: Nc1cc(F)ccc1NC(=O)c1cnc2cc(N3CCNCC3)ccc2n1] | No inhibition | No inhibition | 1301 |
| O | 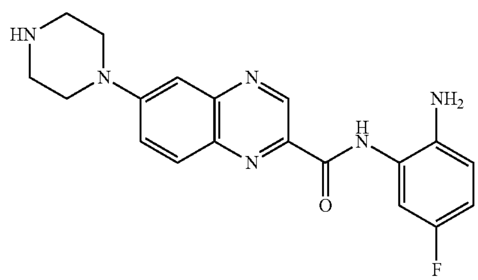 [SMILES: Nc1ccc(F)cc1NC(=O)c1cnc2cc(N3CCNCC3)ccc2n1] | >2000 | >2000 | 675 |
| P | 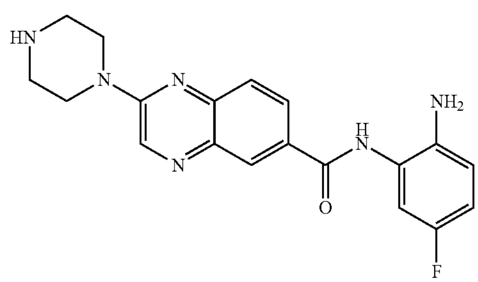 [SMILES: Nc1ccc(F)cc1NC(=O)c1ccc2nc(N3CCNCC3)cnc2c1] | >2000 | 1099 | 235 |
| Q | 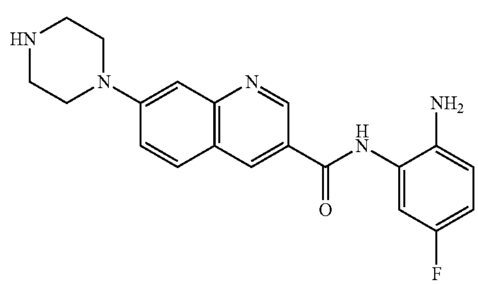 [SMILES: Nc1ccc(F)cc1NC(=O)c1cnc2cc(N3CCNCC3)ccc2c1] | >2000 | >2000 | 308 |

TABLE 1-continued

| Compound ID | Structures | IC 50 (nM) | | |
|---|---|---|---|---|
| | | HDAC1 | HDAC2 | HDAC3 |
| R | [structure: 2-(piperazin-1-yl)quinoline-6-carboxylic acid (2-amino-4-fluorophenyl)amide] | >2000 | 1339 | 315 |

In preferred embodiments, the compounds of the instant invention have one or more of the following properties: the compounds are capable of inhibiting at least one histone deacetylase (HDAC); the compounds are capable of inhibiting HDAC3; the compounds are selective HDAC3 inhibitors.

The invention also provides for a pharmaceutical composition comprising a compound of instant invention, or a pharmaceutically acceptable salt thereof, together with a pharmaceutically acceptable carrier.

Another object of the present invention is the use of a compound as described herein (e.g., of any formulae herein) in the manufacture of a medicament for use in the treatment of a disorder or disease herein. Another object of the present invention is the use of a compound or a composition as described herein (e.g., of any formulae herein) for use in the treatment of a disorder or disease herein.

In another aspect, the invention provides a method of synthesizing a compound of Formula I, II, III, IV, or any of the compounds presented in Table 1. The synthesis of the compounds of the invention can be found in the examples below.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999, and subsequent editions thereof.

Compounds of the present invention can be conveniently prepared or formed during the process of the invention, as solvates (e.g., hydrates). Hydrates of compounds of the present invention can be conveniently prepared by recrystallization from an aqueous/organic solvent mixture, using organic solvents such as dioxan, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). The compounds of this invention may also be represented in multiple tautomeric forms, in such instances, the invention expressly includes all tautomeric forms of the compounds described herein. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of the Invention

In one aspect, the invention provides a method of inhibiting HDAC3 in a subject, comprising administering a compound of Formula I, II, III, IV, or any of the compounds presented in Table 1, or a pharmaceutically acceptable salt thereof.

In another aspect, the invention provides a method of selectively inhibiting HDAC3 over other HDACs in a subject, comprising administering a compound of Formula I, II, III, IV, or any of the compounds presented in Table 1, or a pharmaceutically acceptable salt thereof.

In one embodiment, the compound has a selectivity of 5 to 1000 fold for HDAC3. In another embodiment, the compound has a selectivity for HDAC3 when tested in a HDAC enzyme assay of about 5 to 1000 fold.

In another aspect, the invention provides a method of treating a disease mediated by HDAC3 in a subject comprising administering to the subject a compound of Formula I, II, III, IV, or any of the compounds presented in Table 1, or a pharmaceutical composition thereof.

In yet another aspect, the invention provides a method of treating a disease in a subject comprising administering to the subject a compound of Formula I, II, III, IV, or any of the compounds presented in Table 1, or a pharmaceutical composition thereof.

Inhibition of HDAC3 de-represses γ-globin gene expression and induces production of fetal hemoglobin (HbF). Induction of HbF is an established approach to treat hemoglobinopathy, thalassemia and sickle cell disease (SCD). Thus, the compounds and compositions are capable of de-repressing fetal hemoglobin through HDAC inhibition. In one embodiment, the invention provides a method of treating hemoglobinopathy in a subject comprising administering to the subject a compound of Formula I, II, III, IV, or any of the compounds presented in Table 1, or a pharmaceutical composition thereof. In another embodiment, the invention provides a method of treating sickle cell disease (SCD) in a subject comprising administering to the subject a compound of Formula I, II, III, IV, or any of the compounds presented in Table 1, or a pharmaceutical composition thereof. In yet another embodiment, the invention provides a method of treating thalassemia in a subject comprising administering to the subject a compound of Formula I, II, III, IV, or any of the compounds presented in Table 1, or a pharmaceutical composition thereof.

HDACs also play an important role in cell proliferation and differentiation. Inhibition of HDACs induces apoptosis. Thus HDAC inhibitors can be useful in the treatment of cancers, by effecting tumor cell death or inhibiting the growth of tumor cells. In certain embodiments, to the invention provides a method of treating a cancer or a proliferation disease in a subject comprising administering to the subject a compound of Formula I, II, III, IV, or any of the compounds presented in Table 1, or a pharmaceutical composition thereof.

In another embodiment, the cancer is a hematologic malignancy. The hematologic malignancy can be leukemia or lymphoma. The leukemia can further be acute lymphoblastic leukemia (ALL), acute myelogenous leukemia (AML), chronic lymphocytic leukemia (CLL), chronic myelogenous leukemia (CML), acute monocytic leukemia (AML), or acute promyelocytic leukemia (APL). The lymphoma can be Hodgkin's lymphoma or Non-Hodgkin's lymphoma.

In yet another embodiment, the cancer is a solid tumor. The solid tumor can be a brain tumor, neuroblastoma, retinoblastoma, Wilm's tumor, bone tumors, soft-tissue sarcomas, head cancer, neck cancer, gastric cancer, prostate cancer, bladder cancer, renal cancer, cancer of the uterus, ovarian cancer, testicular cancer, colon cancer, lung cancer, or breast cancer. The solid tumor can also be gastric cancer, prostate cancer, or colon cancer.

Furthermore, HDAC inhibitors have been found to be protective in different cellular and animal models of acute and chronic neurodegenerative diseases. Thus, in one embodiment, the invention provides a method of treating a neurodegenerative disease in a subject comprising administering to the subject a compound of Formula I, II, III, IV, or any of the compounds presented in Table 1, or a pharmaceutical composition thereof.

In certain embodiments, the neurodegenerative disease is Huntington's disease, Friedrich's ataxia, myotonic dystrophy, Parkinson's disease, spinocerebellar ataxia, Kennedy's disease, amyotrophic lateral sclerosis, spinal and bulbar muscular atrophy, or Alzheimer's disease.

HDAC inhibitors have been demonstrated to be able to reduce memory deficits and neurodegeneration. In particular, inhibition of HDAC3 is found to significantly enhance long-term memory. Thus, in one embodiment, the invention provides a method of treating a disease which causes memory deficits comprising administering to the subject a compound of Formula I, II, III, IV, or any of the compounds presented in Table 1, or a pharmaceutical composition thereof.

Class I HDAC inhibitors have also been demonstrated to reduce body weight and glucose and insulin levels in obese diabetic mice, and are suggested to be potential therapeutics for type 2 diabetes. Thus, in one embodiment, the invention provides a method of treating metabolic disease in a subject comprising administering to the subject a compound of Formula I, II, III, IV, or any of the compounds presented in Table 1, or a pharmaceutical composition thereof.

In certain embodiment, the invention provides a method of treating type 2 diabetes in a subject comprising administering to the subject a compound of Formula I, II, III, IV, or any of the compounds presented in Table 1, or a pharmaceutical composition thereof.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Also, as discussed above, the compounds of the invention are selective inhibitors of HDAC3 and, as such, are useful in the treatment of disorders modulated by these histone deacetylases (HDACs). For example, compounds of the invention may be useful in the treatment of cancer (e.g., lung cancer, colon cancer, breast cancer, leukemia, or lymphomas, etc.). Accordingly, in yet another aspect, according to the methods of treatment of the present invention, tumor cells are killed, or their growth is inhibited by contacting said tumor cells with an inventive compound or composition, as described herein.

Thus, in another aspect of the invention, methods for the treatment of cancer are provided comprising administering a therapeutically effective amount of an inventive compound (i.e., of any of the formulae herein), as described herein, to a subject in need thereof. In certain embodiments, the subject is identified as in need of such treatment. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, can be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer and other proliferative disorders including, but not limited to lung cancer (e.g. non-small cell lung cancer), colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, gliobastoma, hepatocellular carcinoma, papillary renal carcinoma, head and neck squamous cell carcinoma, leukemia (e.g., CML, AML, CLL, ALL), lymphomas (non-Hodgkin's and Hodgkin's), myelomas, retinoblastoma, cervical cancer, melanoma and/or skin cancer, bladder cancer, uterine cancer, testicular cancer, esophageal cancer, and solid tumors.

In certain embodiments, the invention provides a method of treatment of any of the disorders described herein, wherein the subject is a human.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight (0.05 to 4.5 mg/m$^2$). An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg (about 0.18 mg/m$^2$ to about 900 mg/m$^2$), alternatively from about 1 to about 50 mg/kg (about 1.8 to about 90 mg/m$^2$). In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Pharmaceutical Compositions

In another aspect, the invention provides a pharmaceutical composition comprising any of the compounds of the instant invention (Formula I, II, III, IV, or any of the compounds presented in Table 1) or a pharmaceutically acceptable salt thereof, together with a pharmaceutically acceptable carrier.

The pharmaceutical compositions of the present invention comprise a therapeutically effective amount of a compound of the present invention formulated together with one or more pharmaceutically acceptable carriers. The term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Definitions of variables in the structures in schemes herein are commensurate with those of corresponding positions in the formulae delineated herein.

Example 1

Synthesis of Compound G

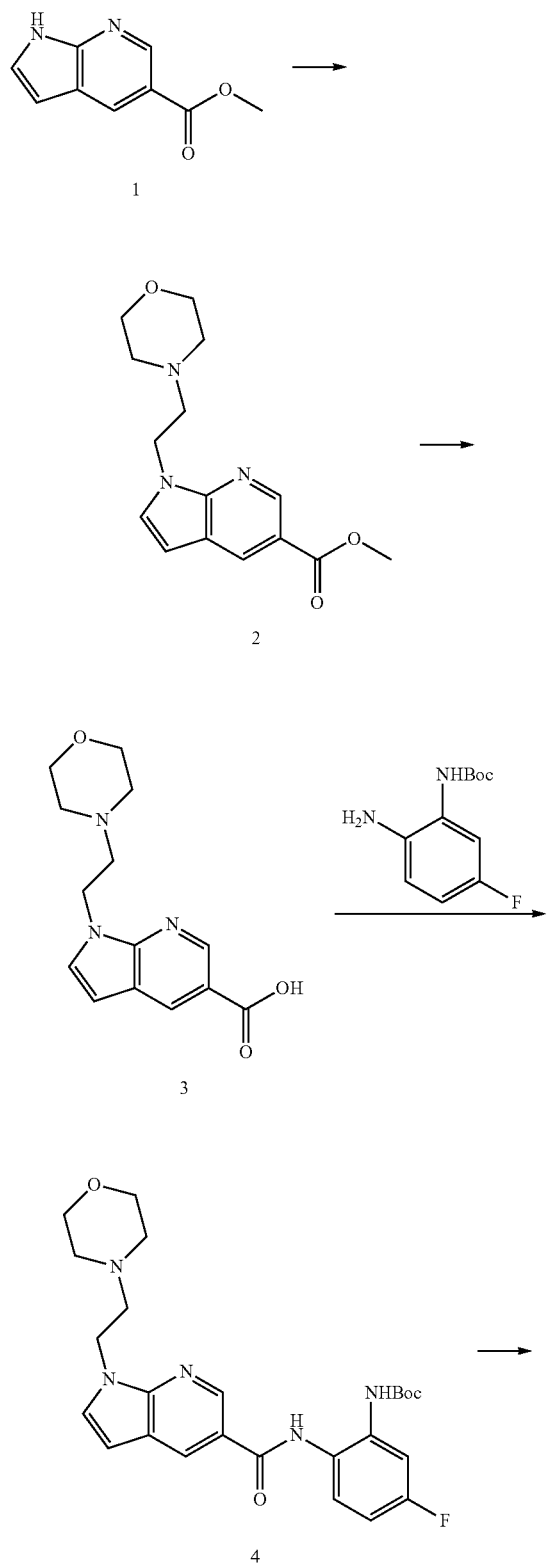

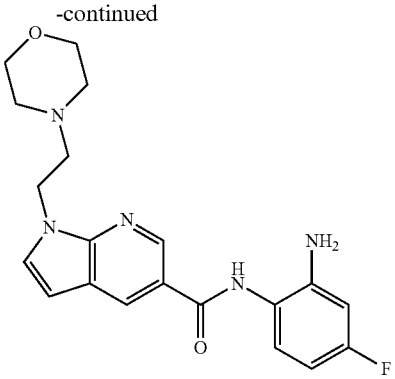

Step 1: A mixture of compound 1 (280 mg, 1.59 mmol), 4-(2-chloroethyl)morpholine (474 mg, 3.18 mol), and KOH (267 mg, 4.77 mmol) in DMSO (5 ml) was stirred at 55° C. for 2 h. TLC was used to monitor the reaction. To the mixture was added water (10 ml), extracted with EA (10 ml×2), separated, dried, filtered and concentrated to get compound 2 (300 mg, 65%) as light red solid.

Step 2: A mixture of compound 2 (300 mg, 1.4 mmol) and NaOH (2.076 mmol, 83 mg) in EtOH (10 mL) was stirred at 60° C. for 3 h. The mixture was concentrated to get a residue, to which was added sat. citric acid (10 ml), extracted with EA (25 ml×2), separated organic layer, dried, filtered and concentrated to get compound 3 (210 mg, 74%) as a light yellow solid.

Step 3: A mixture of compound 3 (210 mg, 0.7 mmol), amine (199 mg, 0.7 mmol), HOAT (220 mg, 1.05 mmol), EDCI (269 mg, 1.4 mmol), DIPEA (271 mg, 2.1 mmol) in DMF (5 ml) was stirred at 55° C. for overnight. To the mixture was added water (10 mL), extracted with EA (15 ml×2), the organic layer was separated, dried, filtered and concentrated to get a residue, which was purified by Pre-TLC to afford compound 4 (180 mg, 47%) as yellow solid.

Step 4: To a solution of compound 6 (180 mg, 0.37 mmol) in DCM (10 ml) was added TFA (2 mL), the reaction was stirred at rt for 2 h. The mixture was worked up and purified by prep-HPLC to afford Compound G as a white solid (10 mg, 7%) LCMS: m/z=384 (M+H)

Example 2

Synthesis of Compound I

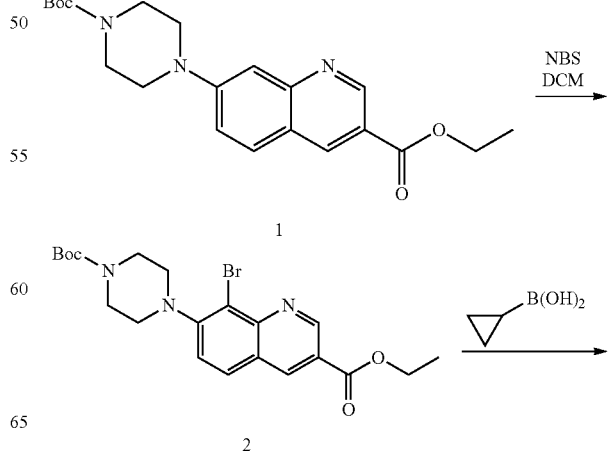

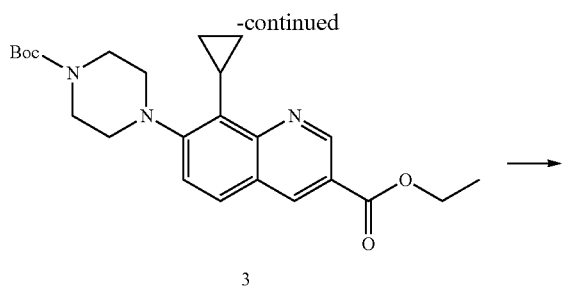

mL×2), the organic layer was separated, dried, filtered and concentrated to get a residue, which was purified by Pre-TLC to afford compound 5 (145 mg, 80%) as yellow solid.

Step 5: A solution of compound 5 (100 mg, 0.00016 mol) in DCM (3 mL) was added TFA 1.5 mL) and stirred at rt for 1 h. The mixture was worked up and concentrated to get a residue, which was purified by Pre-HPLC to afford Compound I (40 mg, 60%) as white solid.

Example 3

Synthesis of Compound C

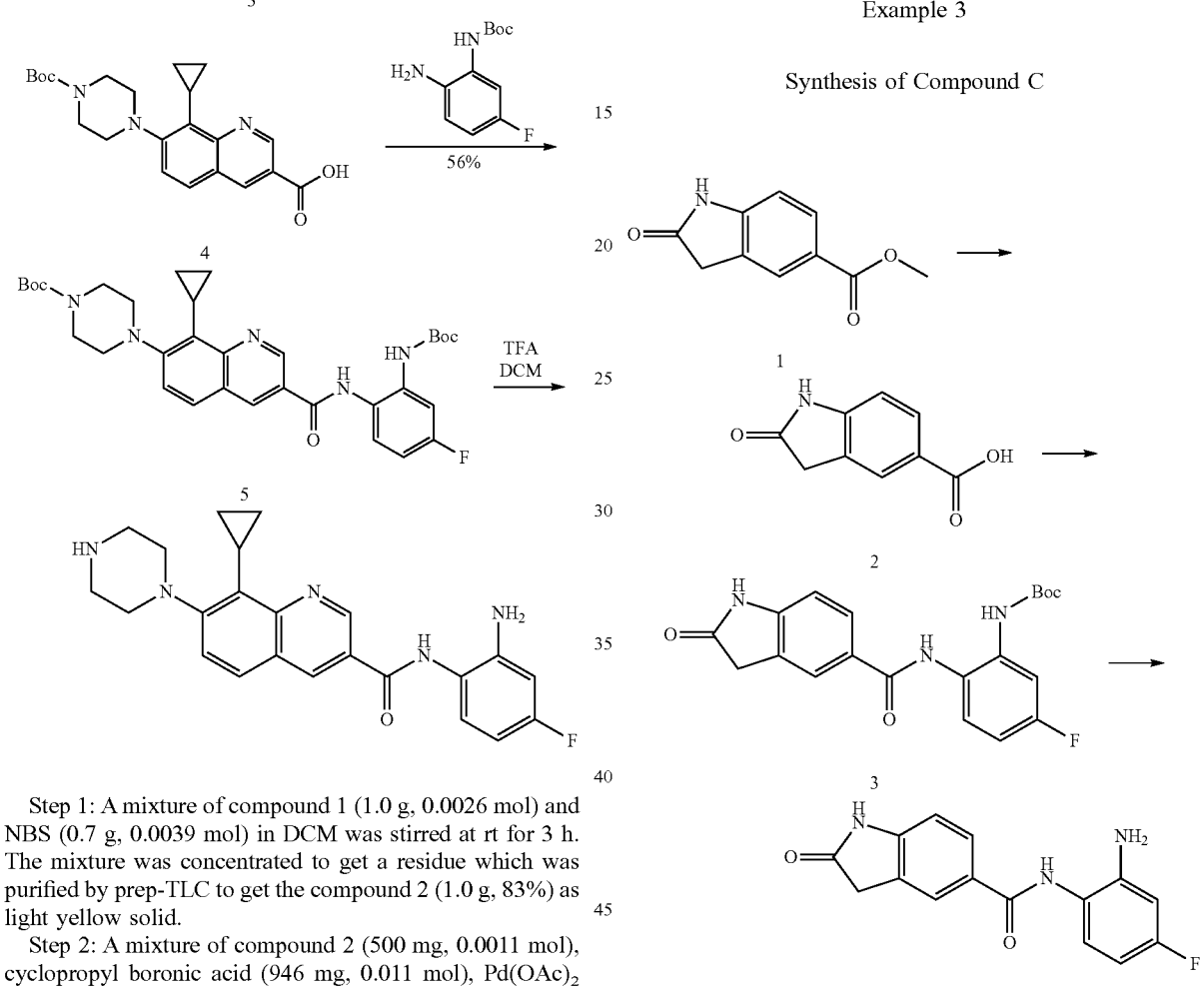

Step 1: A mixture of compound 1 (1.0 g, 0.0026 mol) and NBS (0.7 g, 0.0039 mol) in DCM was stirred at rt for 3 h. The mixture was concentrated to get a residue which was purified by prep-TLC to get the compound 2 (1.0 g, 83%) as light yellow solid.

Step 2: A mixture of compound 2 (500 mg, 0.0011 mol), cyclopropyl boronic acid (946 mg, 0.011 mol), Pd(OAc)$_2$ (25 mg, 0.00011 mol), tricyclohexylphosphine (61 mg, 0.00022 mol) and K$_3$PO$_4$ (933 mg, 0.0044 mol) in toluene (20 mL) and water (3 mL) was stirred at 100° C. under N$_2$ atmosphere overnight. The mixture was cooled, filtered, concentrated to get a residue, which was purified by Pre-TLC to get the compound 3 (370 mg, 81%) as light yellow solid.

Step 3: A mixture of compound 3 (300 mg, 0.0007 mol) and NaOH (2M, 5 mL) in EtOH (15 mL) and THF (15 mL) was stirred at 60° C. for 5 h. The mixture was concentrated to get a residue, which was added sat. citric acid (10 mL), extracted with EA (25 mL×2), separated organic layer, dried, filtered and concentrated to get compound 4 (195 mg, 70%) as light yellow solid.

Step 4: A mixture of compound 4 (120 mg, 0.0003 mol), amine (68 mg, 0.0003 mol), HOAT (61 mg, 0.00045 mol), EDCI (115 mg, 0.0006 mol), DIPEA (155 mg, 0.0012 mol) in DMF (5 mL) was stirred at 55° C. for overnight. To the mixture was added water (20 mL), extracted with EA (25

Step 1: A mixture of compound 1 (200 mg, 1.0 mmol) and HCl (2.0 M in H2O, 5 mL) was heated to 100° C. for overnight. The mixture was concentrated to get compound 2 (180 mg, 97%) as light yellow solid.

Step 2: A solution of compound 2 (90 mg, 0.5 mmol), EDCI (192 mg, 1.0 mmol), HOAT (136 mg, 1.0 mmol) and DIPEA (0.5 mL) in DMF (3 mL) was stirred at rt for 10 min, amine (115 mg, 0.5 mmol) was added, then the mixture was heated to 60° C. for overnight. The reaction was quenched with water and the precipitate was collected to afford compound 3 (100 mg, 41%) as brown solid Step 3: To a solution of compound 3 (100 mg, 0.25 mmol) in DCM (3 mL) was added TFA (0.6 mL) at 0° C., and then the reaction solution was stirred at rt for 45 mins. The mixture was concentrated to get a residue, which was purified by prep-HPLC to afford Compound C (5 mg, 7%) as white solid.

Example 4

Synthesis of Compound A

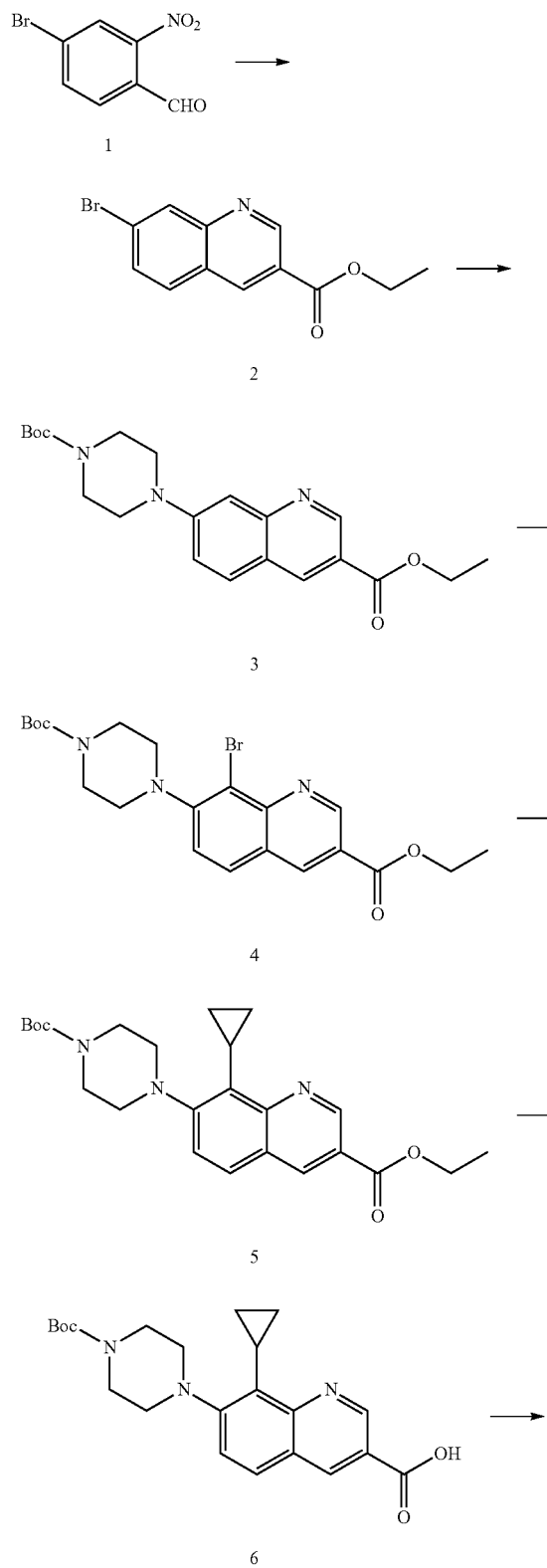

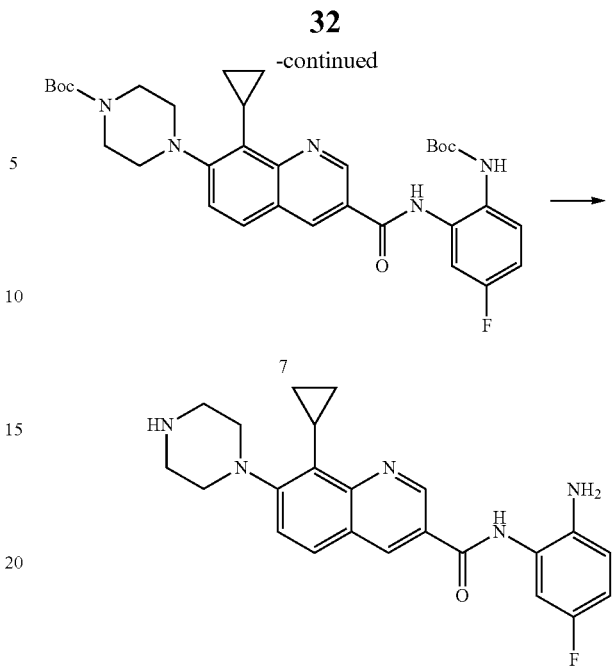

Step 1: To a solution of compound 1 (20 g, 0.087 mol) and SM-1 (33 g, 0.17 mol) in EtOH (500 mL) was added $SnCl_2 \cdot 2H_2O$ (87 g, 0.39 mol), the mixture was stirred at 90° C. for 12 h. TLC was used to monitor the reaction. The mixture was cooled and evaporated to get the crude product. Added EA (600 mL), H2O (300 mL), $Na_2CO_3$ (32 g) and stirred for 1 h. The organic layer was separated, dried, filtered and concentrated to get compound 2 (15 g, 92%) as yellow solid.

Step 2: A mixture of compound 2 (560 mg, 2 mmol), N-boc-piperazine (1.3 g, 7 mmol), $Pd_2(dba)_3$ (200 mg, 0.2 mmol), Ruphos (200 mg, 0.4 mmol), and $Cs_2CO_3$ (1.4 g, 7.3 mmol) in Toluene (20 mL) was microwaved at (80° C. 10 min, 110° C. 30 min, 145° C. 60 min). TLC was used to monitor reaction. To the mixture was added EA (30 mL), and $H_2O$ (30 mL). The organic layer was separated, washed, dried, filtered and concentrated, petroleum ether (PE) to wash it, get purified compound 3 (620 mg, ~100%) as yellow solid.

Step 3: To a solution of compound 3 (2.48 g, 6.44 mmol) in 20 ml DCM was added NBS (1.72 g, 9.66 mmol). The mixture was stirred at 0° C. for 2 h TLC monitored reaction completion. Evaporating to get the crude product, then purified by silica gel column to get compound 4 (1.8 g, 63.6%)

Step 4: To a solution of compound 4 (2 g, 4.32 mmol) and cyclopropylboronic acid (928.7 mg, 10.8 mmol) in 20/20 ml tolune/$H_2O$ was added TCP (123.2 mg, 0.44 mmol), $Pd(OAc)_2$ (98.6 mg, 0.44 mmol), $K_3PO_4$ (2.75 g, 13.0 mmol). The mixture was stirred at 100° C. for overnight. LCMS was used to monitor the reaction. Extracted with EA, The organic layer was separated, washed, dried, filtered and concentrated, purified by silica gel column to get compound 5 (1 g, 51.8%)

Step 5: A mixture of compound 5 (600 mg, 1.41 mmol) and 2M NaOH (5 ml) in MeOH (10 ml) and THF (10 ml) was stirred 70° C. for 4 h. TLC was used to monitor the reaction. The mixture was concentrated to a residue. Added water (30 mL) and used citric acid to adjust PH to 4-5. Extracted with EA. The organic layer was separated, washed, dried, filtered and concentrated to get compound 6 (500 mg, 89.2%)

Step 6: To a solution of compound 6 (120 mg, 0.30 mmol), amine (70 mg, 0.3 mmol) in 10 ml DMF was added HOAT (81.6 mg, 0.6 mmol), EDCI (114.6 mg, 0.6 mmol), DIPEA (193.5 mg, 1.5 mmol). The mixture was stirred at 60° C. for overnight LCMS monitored the reaction completion. Added water (10 ml) extracted with EA. The organic layer was separated, washed, dried, filtered and concentrated to get crude product, Purified by prep-TLC to get compound 7 (100 mg, 54.8%)

Step 7: A mixture of compound 7 (100 mg, 0.16 mmol) and 2 ml TFA in 5 ml DCM was stirred rt for 2 h, LCMS was used to monitor the reaction. Evaporated to get crude product, and purified by prep-HPLC to get Compound A (20 mg, 30.8%).

Example 5

Synthesis of Compound J

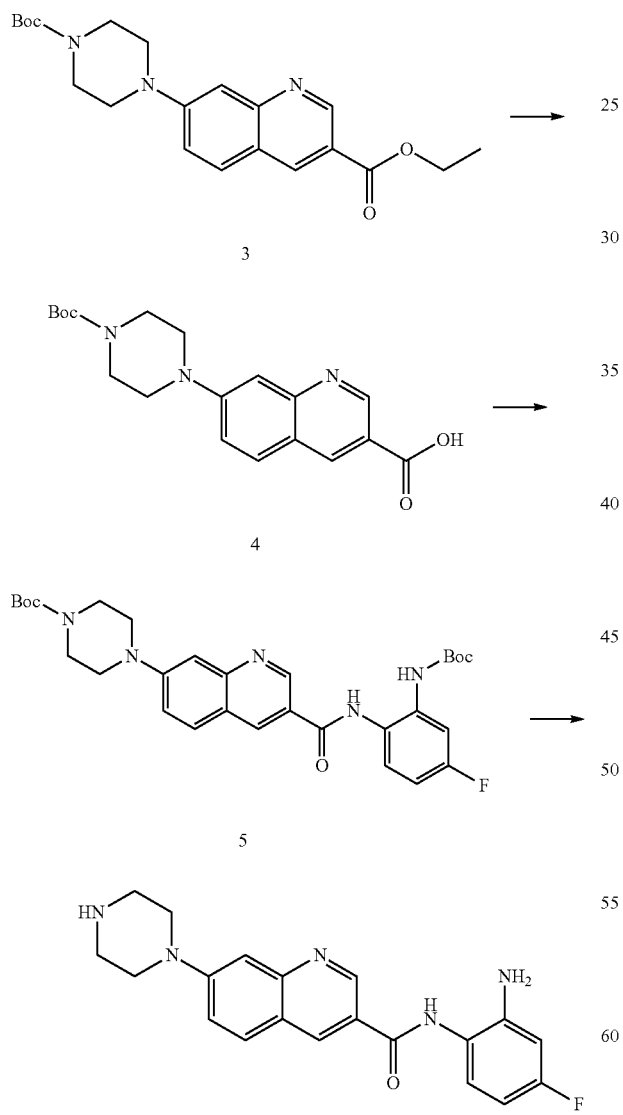

Step 1: A mixture of compound 3 (600 mg, 1.56 mol) and 2M NaOH (5 ml) in MeOH (10 ml) and THF (10 ml) was stirred 70° C. for 4 h. TLC was used to monitor the reaction. The mixture was concentrated to a residue, added water (30 ml) and used citric acid to adjust PH to 4~5. Extracted with EA. The organic layer was separated, washed, dried, filtered and concentrated to get compound 4 (500 mg, 89.2%)

Step 2: To a solution of compound 4 (107 mg, 0.30 mmol) and amine (70 mg, 0.3 mmol) in 10 ml DMF was added HOAT (81.6 mg, 0.6 mmol), EDCI (114.6 mg, 0.6 mmol), and DIPEA (193.5 mg, 1.5 mmol). The mixture was stirred at 60° C. overnight. LCMS was used to monitor the reaction. Added water (10 ml), and extracted with EA. The organic layer was separated, washed, dried, filtered and concentrated to get crude product Purified by prep-TLC to get compound 5 (95 mg, 56%).

Step 3: A mixture of compound 5 (95 mg, 0.16 mmol) and 2 ml TFA in 5 ml DCM was stirred at rt for 2 h. LCMS was used to monitor the reaction. Evaporated to get crude product and purified by prep-HPLC to give Compound J (20 mg, 34.2%).

Example 6

Synthesis of Compound H

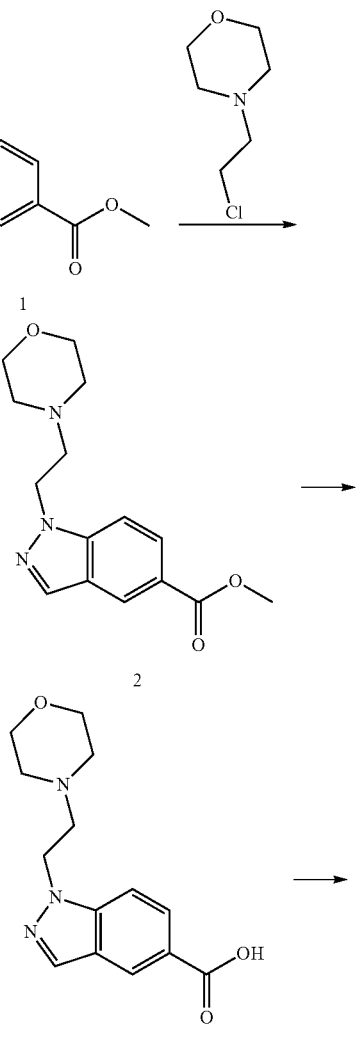

35
-continued

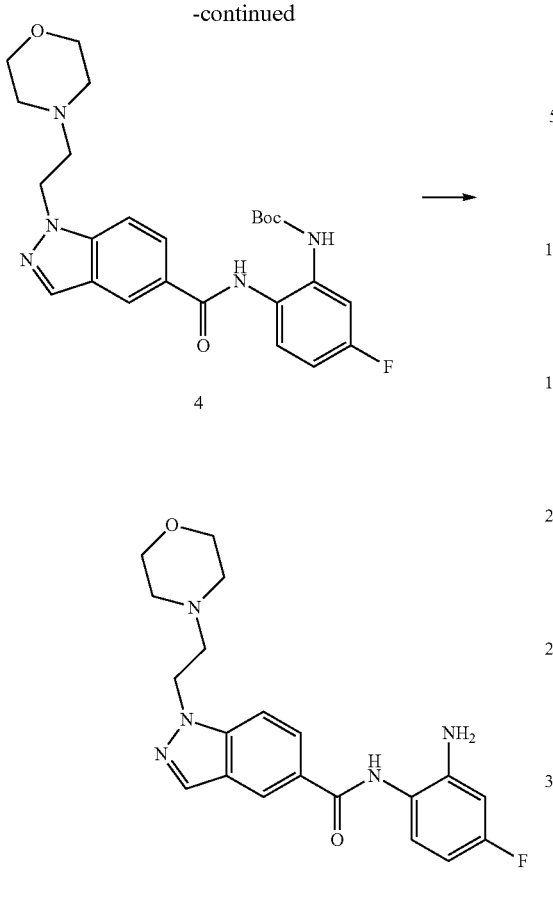

Step 1: To a solution of compound 1 (591 mg, 3.36 mol) and SM-1 (1.0 g, 6.72 mmol) in DMSO (10 mL) was added KOH (376 mg, 6.72 mmol). The mixture was stirred at rt. for 24 h. TLC was used to monitor the reaction. Added water (30 ml) and extracted with EA. The organic layer was separated, washed, dried, filtered and concentrated to get crude product. Purified by silica gel column to get compound 2 (400 mg, 70%)

Step 2: A mixture of compound 2 (400 mg, 1.38 mmol) and 15 ml 2 M HCl was stirred at 100° C. for overnight. LCMS was used to monitor the reaction. Concentrated to get crude product 3 (350 mg, 92.2%)

Step 3: To a solution of compound 3 (82.5 mg, 0.3 mmol), and amine (70 mg, 0.3 mmol) in 10 ml DMF was added HOAT (81.6 mg, 0.6 mmol), EDCI (114.6 mg, 0.6 mmol), DIPEA (193.5 mg, 1.5 mmol). The mixture was stirred at 60° C. for overnight. LCMS was used to monitor the reaction. Added water (10 ml) and extracted with EA. The organic layer was separated, washed, dried, filtered and concentrated to get crude product Purified by prep-TLC to get compound 4 (70 mg, 48%)

Step 4: A mixture of compound 4 (70 mg, 0.15 mmol) and 2 ml TFA in 5 ml DCM was stirred r.t for 2 h. LCMS was used to monitor the reaction. Evaporated to get crude product and purified by prep-HPLC to get Compound H (20 mg, 36.2%)

36

Example 7

Synthesis of Compound B

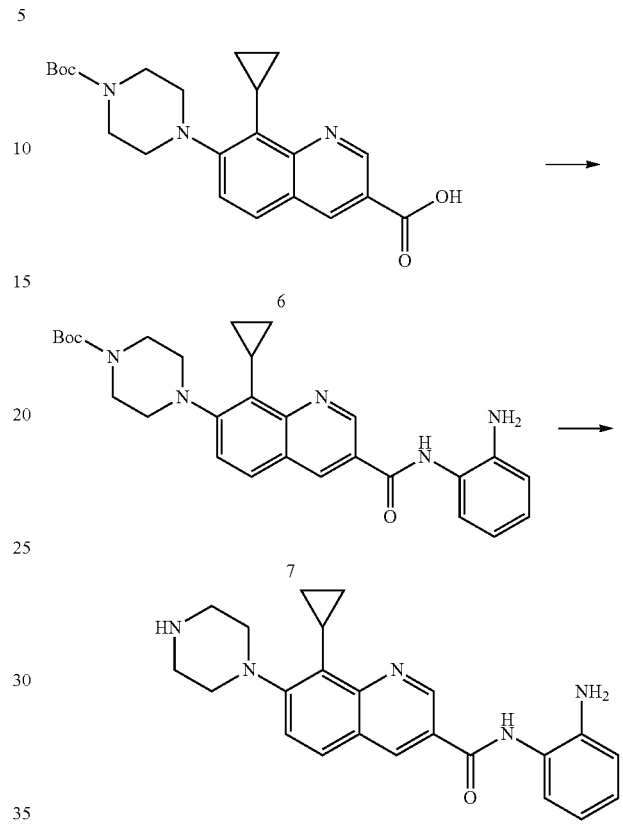

Step 1: To a solution of compound 6 (90 mg, 0.23 mmol), benzene-1,2-diamine (97.9 mg, 0.91 mmol) in 10 ml DMF was added HOAT (61.7 mg, 0.45 mmol), EDCI (86.6 mg, 0.45 mmol), DIPEA (146.2 mg, 1.13 mmol). The mixture was stirred at 60° C. for overnight. LCMS was used to monitor the reaction. Added water (10 ml) and extracted with EA. The organic layer was separated, washed, dried, filtered and concentrated to get crude product and purified by prep-TLC to get compound 7 (90 mg, 87%)

Step 2: A mixture of compound 7 (90 mg, 0.18 mmol) and 2 ml TFA in 5 ml DCM was stirred r.t for 2 h. LCMS was used to monitor the reaction. Evaporated to get the crude residue and purified it by prep-HPLC to get Compound B (15 mg, 24%).

Example 8

Synthesis of Compound E

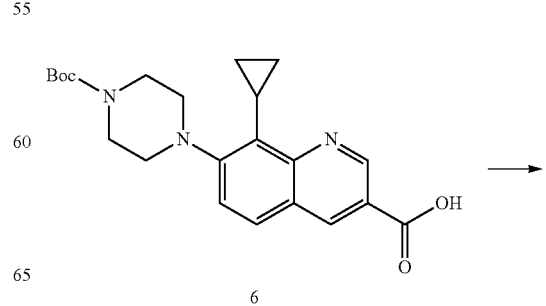

-continued

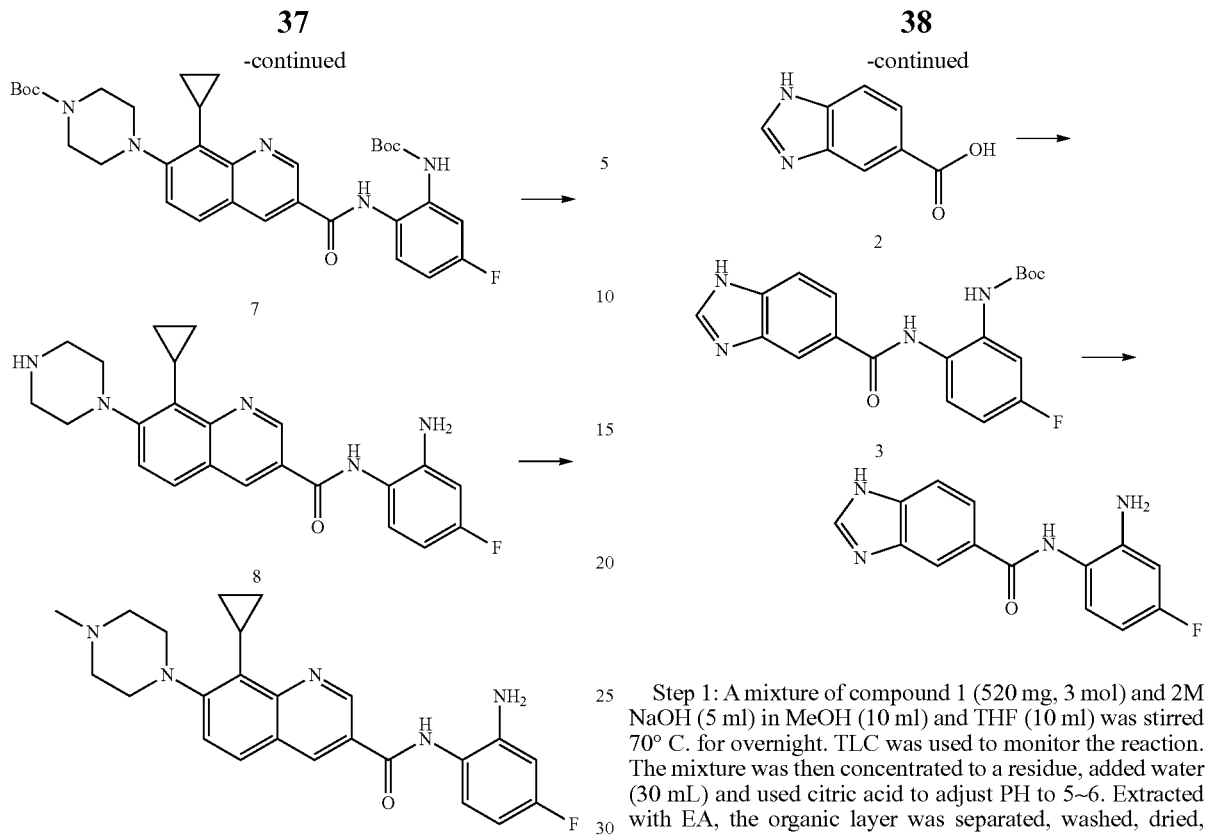

Step 1: To a solution of compound 6 (120 mg, 0.30 mmol), amine (70 mg, 0.3 mmol) in 10 ml DMF was added HOAT (81.6 mg, 0.6 mmol), EDCI (114.6 mg, 0.6 mmol), DIPEA (193.5 mg, 1.5 mmol). The mixture was stirred at 60° C. for overnight. LCMS was used to monitor the reaction. Added water (10 ml) and extracted with EA. The organic layer was separated, washed, dried, filtered and concentrated to get a residue and purified it by prep-TLC to get compound 7 (100 mg, 54.8%)

Step 2: A mixture of compound 7 (100 mg, 0.16 mmol) and 2 ml TFA in 5 ml DCM was stirred r.t. for 2 h. LCMS was used to monitor the reaction. Concentrated to get compound 8 (67 mg, 100%)

Step 3: To a solution of compound 8 (30 mg, 0.08 mmol), and $CH_3I$ (12.8 mg, 0.09 mmol) in 5 ml THF was added $Et_3N$ (32.3 mg, 0.32 mmol). The mixture was stirred at r.t. for 2 h. LCMS was used to monitor the reaction. Added 10 ml $H_2O$ and extracted with EA. The organic layer was separated, washed, dried, filtered and concentrated, then purified by prep-HPLC get Compound E (10 mg, 33.3%).

Example 9

Synthesis of Compound D

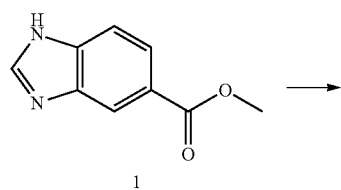

Step 1: A mixture of compound 1 (520 mg, 3 mol) and 2M NaOH (5 ml) in MeOH (10 ml) and THF (10 ml) was stirred 70° C. for overnight. TLC was used to monitor the reaction. The mixture was then concentrated to a residue, added water (30 mL) and used citric acid to adjust PH to 5~6. Extracted with EA, the organic layer was separated, washed, dried, filtered and concentrated to get compound 4 as yellow solid (320 mg, 67%)

Step 2: To a solution of compound 2 (81 mg, 0.5 mmol), and amine (113 mg, 0.5 mmol) in 5 ml DMF was added HOAT (136 mg, 1 mmol), EDCI (191 mg, 1 mmol), DIPEA (260 mg, 2 mmol). The mixture was stirred at 60° C. overnight. LCMS was used to monitor the reaction. Water (10 ml) was added to the reaction mixture and further extracted with EA. The organic layer was separated, washed, dried, filtered and concentrated to get crude product 3 as yellow oil (100 mg, crude)

Step 3: A mixture of compound 3 (100 mg, 00.27 mmol) and 2 ml TFA in 5 ml DCM was stirred at r.t. for 2 h. LCMS was used to monitor the reaction. The mixture was concentrated to yield Compound D which was purified by prep-HPLC (20 mg, 30%).

Example 10

Synthesis of Compound P

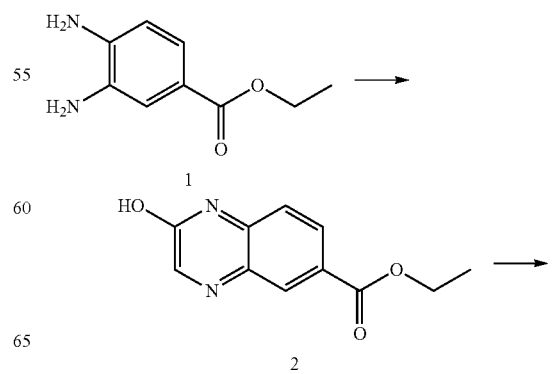

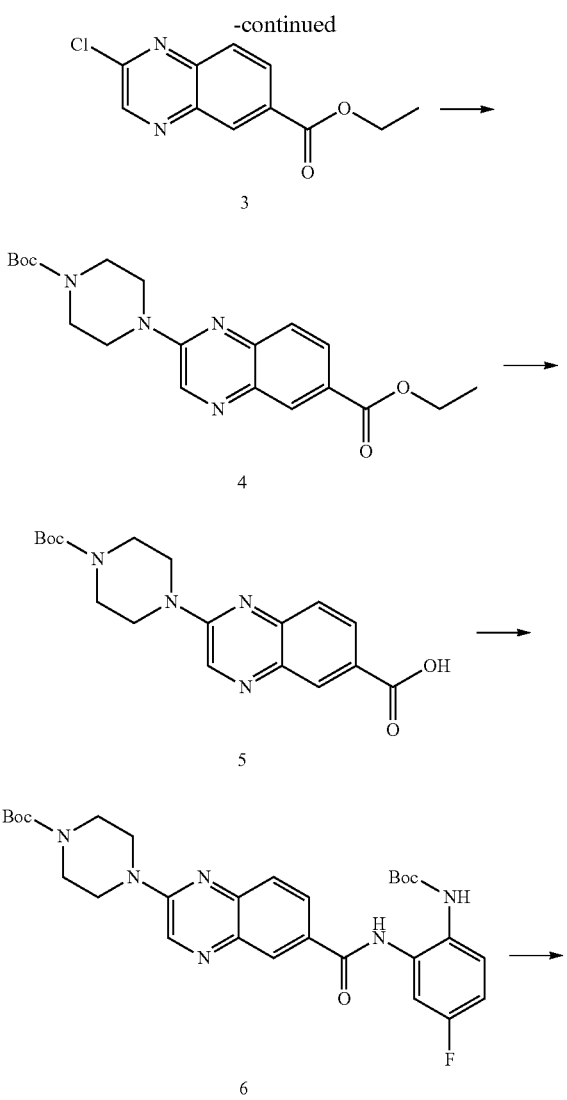

(7.9 g, 0.04 mol), and DIPEA (8.2 g, 0.06 mol) in dioxane was stirred at 100° C. overnight. Water (100 ml) was added to the reaction mixture and extracted with EA (100 ml×2). The organic layer was concentrated to yield a black solid which was used for the next step without any purification (5.5 g, crude).

Step 4: To a solution of ethyl 2-(4-(tert-butoxycarbonyl) piperazin-1-yl)quinoxaline-6-carboxylate (1 g) in EtOH (95%, aq, 5 ml) was added NaOH (2M, aq). The reaction mixture was stirred at 55° C. for 2 hours. The mixture was concentrated and the residue dissolved in water (50 ml). The pH was adjusted to ~7 with citric acid and the solution was extracted with EA (50 ml×3). The organic layer was dried with anhydr-$Na_2SO_4$ and concentrated to yield the target compound as a brown oil (1 g, crude).

Step 5: A solution of 2-(4-(tert-butoxycarbonyl)piperazin-1-yl)quinoxaline-6-carboxylic acid (200 mg, 0.518 mmol), tert-butyl 2-amino-4-fluorophenylcarbamate (117 mg, 0.518 mmol), EDCI (133 mg, 1.036 mmol), HOAt (140 mg, 1.036 mmol), DMAP (6 mg, 0.052 mmol), and DIPEA (133 mg, 1.036 mmol) in DMF (5 ml) was stirred at 55° C. overnight. EA (100 ml) was added, and the resulting solution was washed with water (50 ml×2) and concentrated to yield the target compound as a brown oil (200 mg, crude).

Step 6: To a solution of tert-butyl-4-(6-(2-(tert-butoxycarbonylamino)-5-fluorophenylcarbamoyl)quinoxalin-2-yl) piperazine-1-carboxylate (150 mg) in DCM (2 ml) was added TFA (2 ml). The reaction mixture was stirred at r.t. for 2 hours, concentrated, and purified by Prep-HPLC to obtain the target compound as a yellow solid (53.5 mg, 40%). LCMS: m/z=367.2 (M+H$^+$). $^1$H NMR (500 MHz, DMSO) δ 10.15 (s, 1H), 9.07 (s, 2H), 8.99 (s, 1H), 8.32 (s, 1H), 7.99 (s, 2H), 7.28 (dd, J=10.0, 2.3 Hz, 1H), 7.07-6.93 (m, 2H), 4.09-3.97 (m, 4H), 3.30 (s, 4H).

Example 11

Synthesis of Compound Q

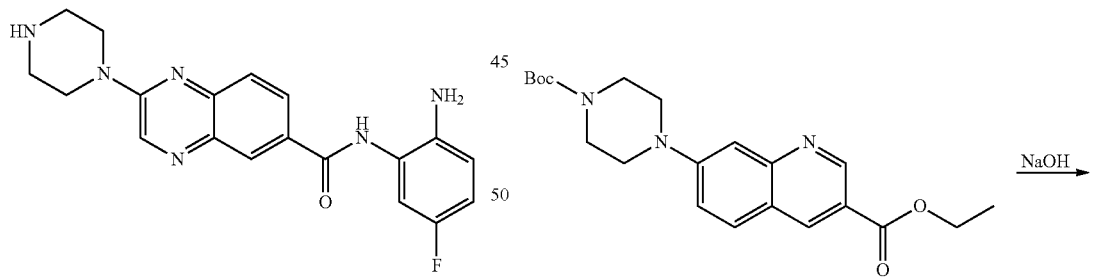

Step 1: To a solution of ethyl 3,4-diaminobenzoate (5 g, 0.027 mol) in EtOH (5 ml) was added ethyl 2-oxoacetate (3.4 g, 0.033 mol), which was then stirred at r.t. for 1 hour. The mixture was concentrated and recrystallized with EtOH to obtain the target compound as a white solid (4.8 g, 80%).

Step 2: A solution of ethyl 2-hydroxyquinoxaline-6-carboxylate (4.8 g) in $POCl_3$ was stirred at 100° C. for 2 hours. The mixture was concentrated and dissolved in EA (100 ml), washed with saturated $NaHCO_3$ solution (50 ml×2), and dried with anhydr-$Na_2SO_4$. Concentration yielded the target compound as a brown solid (5 g, crude).

Step 3: A solution of ethyl 2-chloroquinoxaline-6-carboxylate (5 g, 0.02 mol), tert-butyl piperazine-1-carboxylate

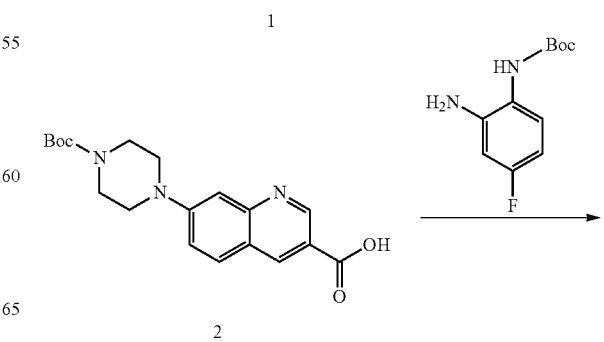

41
-continued

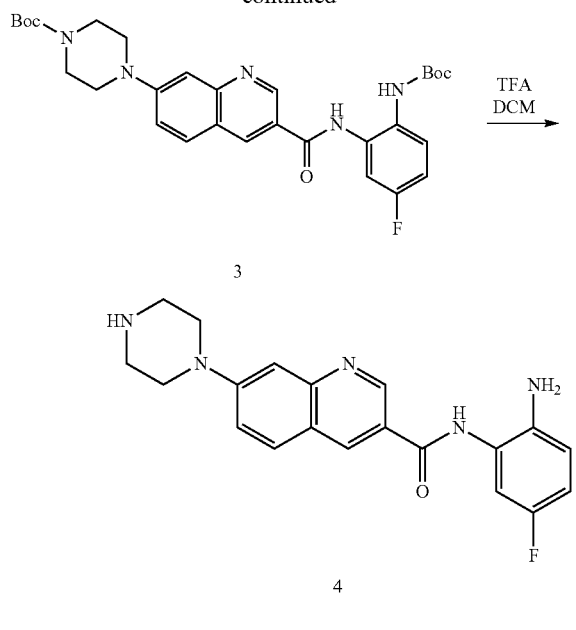

3

4

Step 1: A mixture of ethyl 7-(4-(tert-butoxycarbonyl) piperazin-1-yl)quinoline-3-carboxylate (385 mg, 1 mmol), NaOH (2M, 5 mL) in EtOH (15 mL) and THF (15 mL) was stirred at 60° C. for 5 h. The mixture was concentrated to a residue, to which was added aq. sat. citric acid (10 mL). The solution was extracted with EA (25 mL×2), separated, dried, filtered and concentrated to give the compound 7-(4-(tert-butoxycarbonyl)-piperazin-1-yl)quinoline-3-carboxylic acid (286 mg, 80%) as light yellow solid.

Step 2: A mixture of 7-(4-(tert-butoxycarbonyl)-piperazin-1-yl)quinoline-3-carboxylic acid (214 mg, 0.6 mmol), the amine (136 mg, 0.6 mmol), HOAT (122 mg, 0.9 mmol), EDCI (229 mg, 1.2 mmol), and DIPEA (155 mg, 1.2 mmol) in DMF (5 mL) was stirred at 55° C. overnight. Water (20 mL) was added to the reaction mixture, and followed by extraction with EA (25 mL×2). The combined organic layers were dried, filtered, and concentrated to yield a residue, which was purified by Pre-TLC to afford the compound tert-butyl 4-(3-(2-(tert-butoxycarbonylamino)-5-fluorophenylcarbamoyl) quinolin-7-yl)piperazine-1-carboxylate (220 mg, 65%) as a yellow solid.

Step 3: To a solution of tert-butyl 4-(3-(2-(tert-butoxycarbonylamino)-5-fluoro-phenyl-carbamoyl)quinolin-7-yl) piperazine-1-carboxylate (100 mg, 0.17 mmol) in DCM (3 mL) was added TFA (1.5 mL). The reaction mixture was stirred at r.t for 1 h and concentrated to give a residue, which was purified by Pre-HPLC to afford compound N-(2-amino-5-fluorophenyl)-7-(piperazin-1-yl)quinoline-3-carboxamide (40 mg, 62%) as a light yellow solid. $^1$H NMR (500 MHz, DMSO) δ 10.20 (s, 1H), 9.34 (s, 1H), 9.05 (s, 3H), 8.10 (s, 1H), 7.68 (s, 1H), 7.43 (s, 1H), 7.24 (s, 1H), 6.96 (s, 2H), 3.71 (s, 4H), 3.31 (s, 4H). LCMS: 1.21 min, m/z=366 (M+H)$^+$

42

Example 12

Synthesis of Compound R

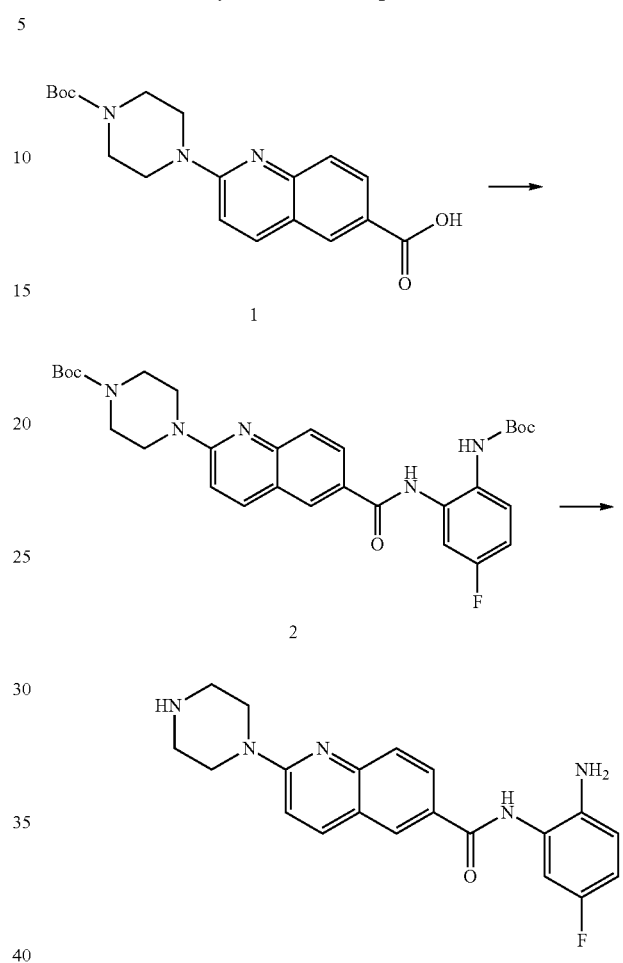

Step 1: A solution of 2-(4-(tert-butoxycarbonyl)piperazin-1-yl)quinoline-6-carboxylic acid (180 mg, 0.5 mmol), tert-butyl 2-amino-4-fluorophenylcarbamate (113 mg, 0.5 mmol), EDCI (129 mg, 1 mmol), and HOAt (136 mg, 1 mmol) in THF (2 ml) was stirred in a sealed tube at 100° C. over night. EA (100 ml) was added to the reaction mixture, followed by washing with water (50 ml×2). The organic layers were concentrated to obtained the target compound as a brown oil (200 mg, crude).

Step 2: To a solution of tert-butyl 4-(6-(2-(tert-butoxycarbonylamino)-5-fluorophenylcarbamoyl)quinolin-2-yl) piperazine-1-carboxylate (200 mg) in DCM (2 ml) was added TFA (2 ml). The reaction mixture was stirred at r.t. for 2 hours, concentrated and purified by Pre-HPLC to obtain the target compound as a yellow solid (40 mg, 60%). LCMS: m/z=366.2 (M+H)+. $^1$H NMR (500 MHz, DMSO) δ 10.09 (s, 1H), 8.99 (s, 2H), 8.47 (d, J=1.6 Hz, 1H), 8.28 (d, J=9.2 Hz, 1H), 8.15 (dd, J=8.8, 1.8 Hz, 1H), 7.70 (d, J=8.8 Hz, 1H), 7.42 (d, J=9.3 Hz, 1H), 7.29 (dd, J=10.1, 2.7 Hz, 1H), 7.11-7.04 (m, 1H), 7.03-6.97 (m, 1H), 4.09-3.89 (m, 4H), 3.27 (s, 4H).

Example 13

Synthesis of Compound K

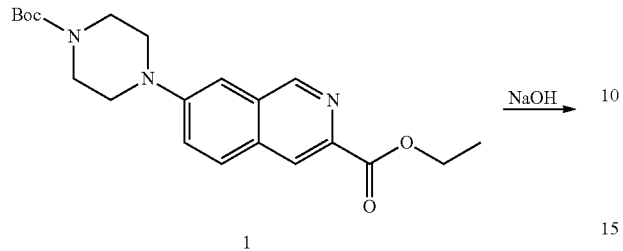

1

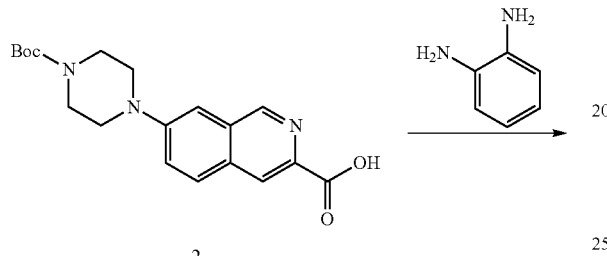

2

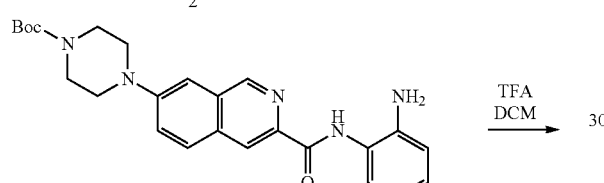

3

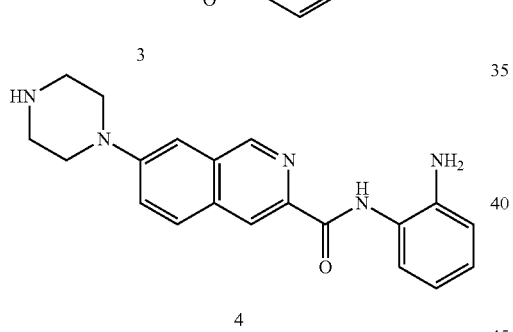

4

Step 1: A mixture of ethyl 7-(4-(tert-butoxycarbonyl)piperazin-1-yl)isoquinoline-3-carboxylate (385 mg, 1 mmol) and NaOH (2M) (5 mL) in EtOH (15 mL) and THF (15 mL) was stirred at 60° C. for 5 h. The mixture was concentrated to a residue, to which was added aq. sat. citric acid (10 mL). The solution was extracted with EA (25 ml×2), separated, dried, filtered and concentrated to yield 7-(4-(tert-butoxycarbonyl)piperazin-1-yl)isoquinoline-3-carboxylic acid (303 mg, 85%) as a light yellow solid.

Step 2: A mixture of 7-(4-(tert-butoxycarbonyl)piperazin-1-yl)isoquinoline-3-carboxylic acid (214 mg, 0.6 mmol), amine (65 mg, 0.6 mmol), HOAT (122 mg, 0.9 mmol), EDCI (229 mg, 1.2 mmol), and DIPEA (155 mg, 1.2 mmol) in DMF (5 mL) was stirred at 55° C. overnight. The mixture was quenched with water (20 mL) and extracted with EA (25 mL×2). The combined organic layers were separated, dried, filtered, and concentrated to a residue, which was purified by Pre-TLC to afford compound tert-butyl 4-(3-(2-aminophenylcarbamoyl)-isoquinolin-7-yl)piperazine-1-carboxylate (201 mg, 75%) as a yellow solid.

Step 3: To a solution of tert-butyl 4-(3-(2-aminophenylcarbamoyl)isoquinolin-7-yl)piperazine-1-carboxylate (100 mg, 0.22 mmol) in DCM (3 mL) was added TFA (1.5 mL). The resulting mixture was stirred at r.t. for 1 h. The mixture was concentrated to a residue, which was purified by Pre-HPLC to afford the desired compound, N-(2-aminophenyl)-7-(piperazin-1-yl)isoquinoline-3-carboxamide (75 mg, 70%) as a light yellow solid. $^1$H NMR (500 MHz, DMSO) δ 10.12 (s, 1H), 9.18 (s, 1H), 8.48 (s, 1H), 8.03 (d, J=9.1 Hz, 1H), 7.73 (d, J=7.0 Hz, 1H), 7.61 (d, J=7.9 Hz, 1H), 7.45 (s, 1H), 6.95 (t, J=7.6 Hz, 1H), 6.85 (d, J=7.8 Hz, 1H), 6.68 (t, J=7.5 Hz, 1H), 4.89 (s, 2H), 3.33-3.12 (m, 4H), 2.93-2.84 (m, 4H). LCMS: 1.69 min, m/z=348 (M+H)$^+$

Example 14

Synthesis of Compound L

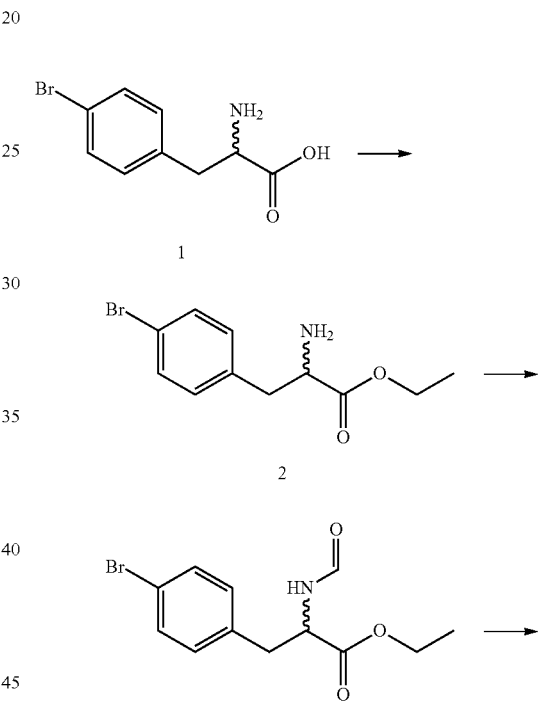

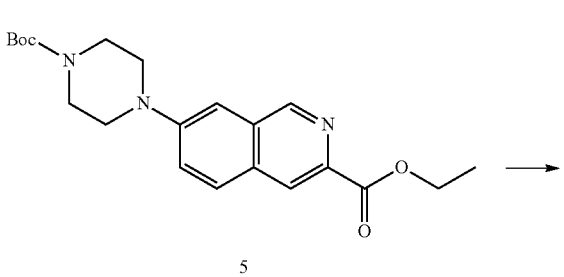

5

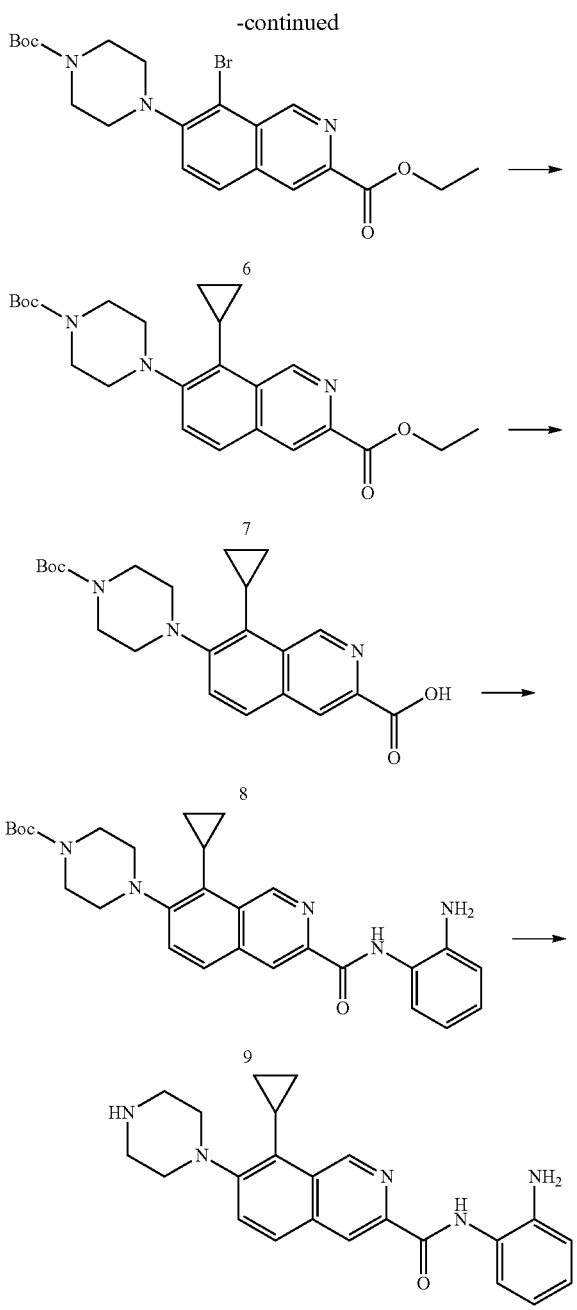

was purified by silica gel chromatography (PE/EA=4:1 to 3:1) to afford ethyl 3-(4-bromophenyl)-2-formamidopropanoate as a red solid (1.7 g, yield: 80%).

Step 3: To a mixture of ethyl-3-(4-bromophenyl)-2-formamidopropanoate (23.5 g, 78 mmol) in DCM (200 mL) was added $(CO)_2Cl_2$ (8 ml, 84 mmol). The reaction mixture was stirred at r.t. for 30 mins. Then the reaction solution was cooled to 0° C. and $FeCl_3$ (16 g, 98 mmol) was added into the solution, followed by stirring at r.t overnight. After the solution was extracted by $CH_2Cl_2$, the combined organic layers were concentrated in vacuo to afford a black oil. The oil was dissolved in the EtOH (100 ml), and concentrated $H_2SO_4$ was added into the solution and refluxed at 80° C. overnight. The solution was poured into saturated $NaHCO_3$ and extracted by EA. After drying with anhydrous $Na_2SO_4$, the solution was concentrated in vacuo, and the residue was purified by silica gel chromatography (PE/EA=8:1 to 5:1) to afford ethyl 7-bromoisoquinoline-3-carboxylate as a yellow solid (5.2 g, yield: 23.8%).

Step 4: A mixture of 7-bromoisoquinoline-3-carboxylate (800 mg, 2.8 mmol), $Pd_2(dba)_3$ (256 mg, 0.28 mmol), Ruphos (162 mg, 0.28 mmol) and $Cs_2CO_3$ (2.73 g, 8.4 mmol) in toluene (20 mL) was stirred at 95° C. under $N_2$ atmosphere overnight. The mixture was filtered, concentrated, and extracted with EA (30 mL×2). The target compound was purified by silica gel chromatography (PE/EA=1:1) to afford ethyl 7-(4-(tert-butoxycarbonyl)piperazin-1-yl)isoquinoline-3-carboxylate as a yellow solid (1.1 g, yield: 99%).

Step 5: To a solution of compound ethyl 7-(4-(tert-butoxycarbonyl)piperazin-1-yl)isoquinoline-3-carboxylate (1.1 g, 2.85 mmol) in DCM (10 mL) was added NBS (508 mg, 2.85 mmol) following by stirring at 0° C. for 1 h. To the reaction mixture was added saturated Na2SO3 (20 ml). The combined organic layers were dried by anhydrous $Na_2SO_4$, concentrated in vacuo, and washed by PE to afford ethyl 8-bromo-7-(4-(tert-butoxycarbonyl)piperazin-1-yl)isoquinoline-3-carboxylate as a light yellow solid (900 mg, yield: 70%).

Step 6: A mixture of ethyl 8-bromo-7-(4-(tert-butoxycarbonyl)piperazin-1-yl)isoquinoline-3-carboxylate (464 mg, 1 mmol), $C_3H_4B(OH)_2$ (860 mg, 10 mmol), $Pd(dppf)Cl_2$ (73 mg, 0.1 mmol) and $K_3PO_4$ (636 mg, 3 mmol) in toluene (20 ml) and $H_2O$ (2 ml) was stirred at 95° C. overnight. After extraction by EA, the residue was dried with anhydrous $Na_2SO_4$, concentrated in vacuo, and purified by silica gel chromatography to afford ethyl-7-(4-(tert-butoxycarbonyl)piperazin-1-yl)-8-cyclopropylisoquinoline-3-carboxylate as a yellow solid (350 mg, yield: 85%).

Step 7: To a solution of compound ethyl 7-(4-(tert-butoxycarbonyl)piperazin-1-yl)-8-cyclopropyl-isoquinoline-3-carboxylate (425 mg, 1 mmol) in EtOH/THF (5 mL) was added NaOH (5 ml, 2 N) followed by stirring for 2 hrs at r.t. After extraction by EA, the residue was concentrated in vacuo to give 7-(4-(tert-butoxycarbonyl)piperazin-1-yl)-8-cyclopropylisoquinoline-3-carboxylic acid as a yellow solid (400 mg, yield: 95%).

Step 8: To a solution of 7-(4-(tert-butoxycarbonyl)piperazin-1-yl)-8-cyclopropylisoquinoline-3-carboxylic acid (60 mg, 0.15 mmol) and o-Phenylenediamine (16 mg, 0.15 mmol) in DMF (5 mL) was added HOAT (41 mg, 0.3 mmol), EDCI (46 mg, 0.3 mmol), and DIPEA (77 mg, 0.6 mmol). The reaction mixture was stirred at 60° C. overnight. After extraction by EA, the combined organic layers were dried by anhydrous $Na_2SO_4$ and concentrated in vacuo to afford Step 1: To a solution of 2-amino-3-(4-bromophenyl)propanoic acid (40 g, 164 mmol) in EtOH (100 mL) was added $SOCl_2$ (30 ml, 422 mmol) dropwise at 80° C. The mixture was stirred at 80° C. for 2 hrs. After the solvent was evaporated, the residue was extracted by EA. The combined organic layers were washed with aqueous NaCl, dried by anhydrous $Na_2SO_4$, and concentrated in vacuo to afford ethyl-2-amino-3-(4-bromophenyl)propanoate as a yellow liquid (32 g, yield: 72%).

Step 2: To a flask containing ethyl 2-amino-3-(4-bromophenyl)propanoate (2 g, 7.4 mmol) in $CH_3CN$ (5 ml) was added $NH_4COOH$ (4 g, 63 mmol) at r.t., followed by stirring at 90° C. overnight. After the solvent was evaporated, the residue was extracted by EA. The combined organic layer was washed with aqueous NaCl, dried by anhydrous $Na_2SO_4$, and concentrated in vacuo. The resulting residue tert-butyl 4-(3-(2-aminophenylcarbamoyl)-8-cyclopropylisoquinolin-7-yl)piperazine-1-carboxylate as a yellow solid (80 mg, yield: 99%).

Step 9: To a solution of tert-butyl 4-(3-(2-aminophenylcarbamoyl)-8-cyclopropylisoquinolin-7-yl)piperazine-1-carboxylate (80 mg, 0.16 mmol) in 5 ml CH$_2$Cl$_2$ was added 0.2 ml TFA followed by stirring at r.t. for 2 hrs. The mixture was concentrated in vacuo. The residue was purified by Pre-HPLC to afford Compound L (10 mg, yield: 16%) as a yellow solid. $^1$H NMR (500 MHz, DMSO): δ 10.37 (s, 1H), 9.88 (s, 1H), 8.93 (br, 2H), 8.57 (s, 1H), 8.08 (d, J=9.5 Hz, 1H), 7.67 (d, J=8.5 Hz, 2H), 7.05 (d, J=22 Hz, 2H), 6.87 (br, 1H), 3.40 (d, J=47.5 Hz, 8H), 2.26 (s, 1H), 1.33 (d, J=6.5 Hz, 2H), 0.77 (d, J=4.0 Hz, 2H). LCMS: m/z=388 (M+H)$^+$.

Example 15

Synthesis of Compound M

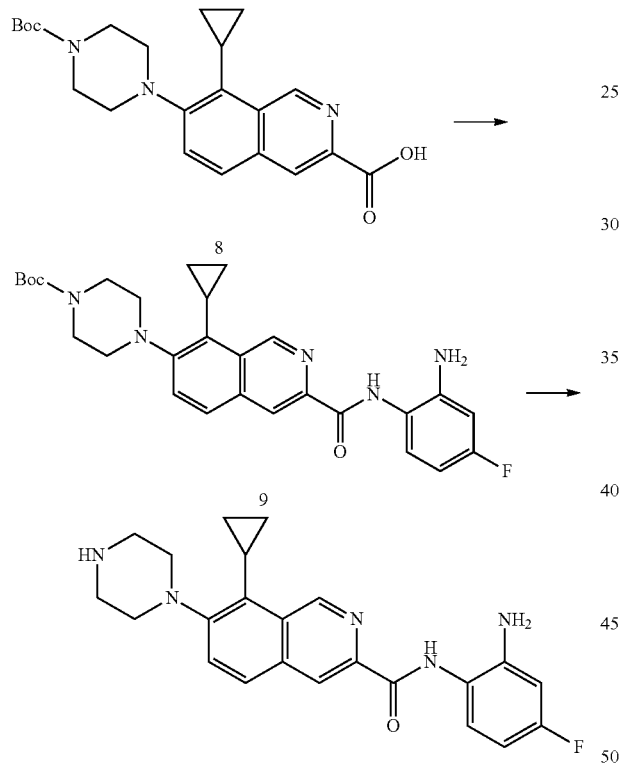

Step 1: To a mixture of 7-(4-(tert-butoxycarbonyl)piperazin-1-yl)-8-cyclopropylisoquinoline-3-carboxylic acid (60 mg, 0.15 mmol), EDCI (36 mg, 0.23 mmol), HOAT (32 mg, 0.23 mmol) in DMF (2 mL) was added DIPEA (39 mg, 0.3 mmol) and amine (34 mg, 0.15 mmol). The reaction mixture was heated to 60° C. and stirred overnight. The mixture was washed with water, extracted with EA, purified by gel chromatography (PE:EA=2:1) to afford tert-butyl 4-(3-(2-amino-4-fluorophenylcarbamoyl)-8-cyclopropylisoquinolin-7-yl)piperazine-1-carboxylate (60 mg, yield: 62%) as a yellow solid.

Step 2: To a solution of tert-butyl 4-(3-(2-amino-4-fluorophenylcarbamoyl)-8-cyclopropylisoquinolin-7-yl)piperazine-1-carboxylate (60 mg, 0.1 mmol) in DCM (2 mL) was added TFA (0.2 mL) at 0° C. The reaction solution was stirred at r.t. for 45 mins and then concentrated to a residue. Purification of the residue by prep-HPLC afforded Compound M (27 mg, yield: 66%) as yellow solid. $^1$H NMR (500 MHz, DMSO): δ 10.12 (s, 1H), 9.88 (s, 1H), 8.81 (br, 2H), 8.54 (s, 1H), 8.08 (d, J=9 Hz, 1H), 7.67 (d, J=29 Hz, 1H), 7.49 (d, J=12 Hz, 1H), 7.43 (br, 1H), 6.64 (d, J=3.5 Hz, 1H), 6.43 (br, 1H), 3.42 (d, J=2.5 Hz, 4H), 3.34 (d, J=0.5 Hz, 4H), 2.23 (s, 1H), 1.30 (d, J=15.5 Hz, 2H), 0.77 (d, J=15.0 Hz, 2H). LCMS: m/z=406 (M+H)+.

Example 16

Synthesis of Compound N

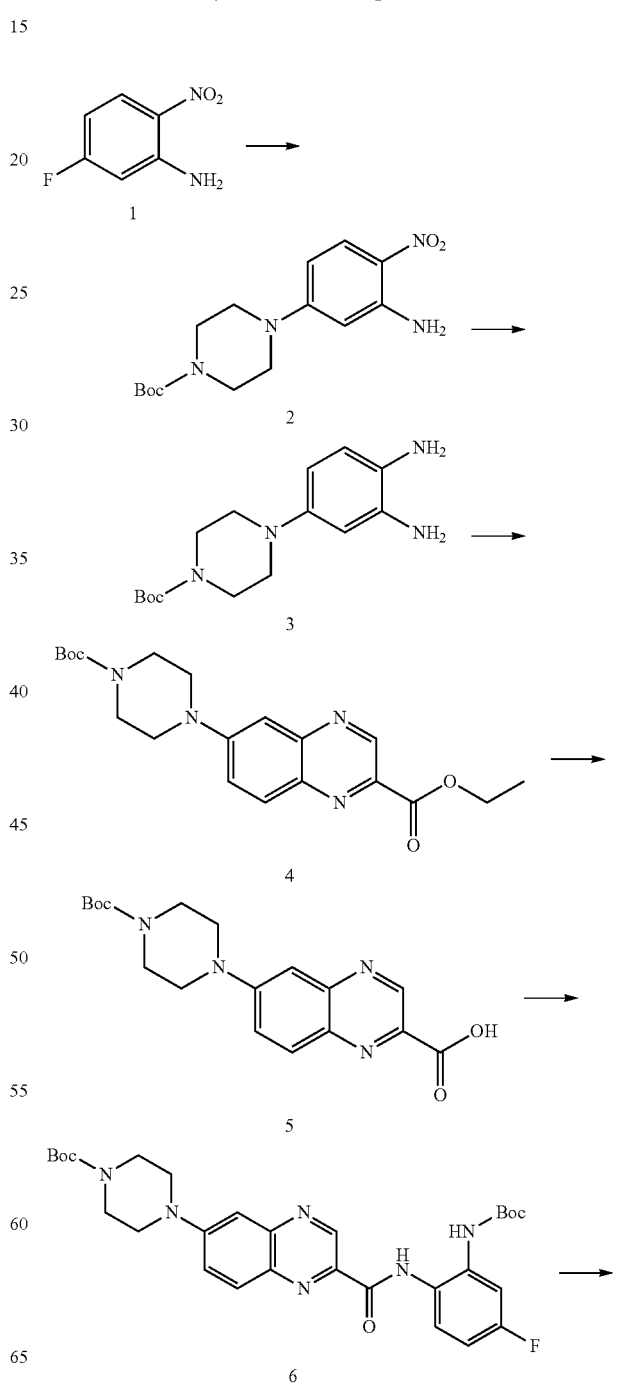

-continued

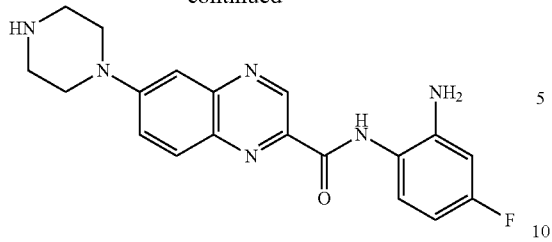

Step 1: To a solution of 5-fluoro-2-nitroaniline (10 g, 64.1 mmol) in DMF (65 mL) was added tert-butyl-piperazine carboxylate (13.1 g, 70.5 mmol) and K$_3$PO$_4$ (13.3 g, 96.2 mmol). The reaction mixture was stirred at 100° C. overnight. After adding 100 ml H$_2$O into the solution, the precipitated yellow solid was filtered under vacuum then dried in vacuo to afford tert-butyl 4-(3-amino-4-nitrophenyl)piperazine-1-carboxylate as yellow solid (15 g, yield: 82%).

Step 2: A mixture of tert-butyl-4-(3-amino-4-nitrophenyl)piperazine-1-carboxylate (13 g, 46 mmol), Zn (8.9 g, 140 mmol), and HOAc (8.4 g, 140 mmol) in EtOH/THF (250 ml) was refluxed for 20 mins. After adjusted its PH to 8 by NaHCO$_3$, EA and H$_2$O were added resulting in a precipitate. The solid was filtered off under vacuum. The combined organic layers were dried by anhydrous Na$_2$SO$_4$ and concentrated in vacuo to afford tert-butyl 4-(3,4-diaminophenyl)piperazine-1-carboxylate as a black solid (8 g, yield: 60%).

Step 3: A mixture of tert-butyl-4-(3,4-diaminophenyl)piperazine-1-carboxylate (8 g, 27.6 mmol), Ethyl bromopyruvate (8 g, 41.4 mmol), and NMP (40 ml) was stirred at r.t. overnight. The solution was extracted by EA and purified by gel chromatography (PE:EA=3:1) to afford ethyl 6-(4-(tert-butoxycarbonyl)piperazin-1-yl)quinoxaline-2-carboxylate (2 g, yield: 20%) as a yellow solid.

Step 4: To a solution of ethyl 6-(4-(tert-butoxycarbonyl)piperazin-1-yl)quinoxaline-2-carboxylate (500 mg, 1.3 mmol) in EtOH/THF (5 mL) was added NaOH (5 ml, 2 mmol) followed by stirring for 2 hrs at r.t. After extraction by EA, the combined organic layers were concentrated in vacuo to yield 6-(4-(tert-butoxycarbonyl)piperazin-1-yl)quinoxaline-2-carboxylic acid as a red solid (260 mg, yield: 56%).

Step 5: To a mixture of 6-(4-(tert-butoxycarbonyl)piperazin-1-yl)quinoxaline-2-carboxylic acid (150 mg, 0.42 mmol), EDCI (130 mg, 0.84 mmol), HOAT (114 mg, 0.84 mmol), in DMF (5 mL) was added DIPEA (217 mg, 1.68 mmol) and amine (95 mg, 0.42 mmol). The reaction mixture was heated to 60° C. overnight. Water was added to the mixture and the resulting solution was extracted with EA, dried by anhydrous Na$_2$SO$_4$, and concentrated in vacuo to afford tert-butyl 4-(2-(2-(tert-butoxycarbonylamino)-4-fluoro-phenylcarbamoyl)-quinoxalin-6-yl)-piperazine-1-carboxylate as a black solid (160 mg, yield: 67%).

Step 6: To a solution of tert-butyl 4-(2-(2-(tert-butoxycarbonylamino)-4-fluorophenyl-carbamoyl)quinoxalin-6-yl)piperazine-1-carboxylate (50 mg, 0.09 mmol) in 5 ml CH$_2$Cl$_2$ was added 0.2 ml TFA followed by stirring at r.t for 2 hrs. The mixture was concentrated in vacuo and the residue was purified by Pre-HPLC to afford Compound N (10 mg, 30%) as a yellow solid. $^1$H NMR (500 MHz, DMSO): δ 9.98 (s, 1H), 9.21 (s, 1H), 8.24 (s, 1H), 8.00 (d, J=9.5 Hz, 1H), 7.87 (d, J=9.5 Hz, 1H), 7.32 (m, 2H), 6.58 (d, J=11.5 Hz, 1H), 6.40 (t, J=17 Hz, 1H), 5.33 (br, 2H), 3.43 (s, 4H), 2.99 (s, 4H), LCMS: m/z=367 (M+H)$^+$.

Example 17

Synthesis of Compound O

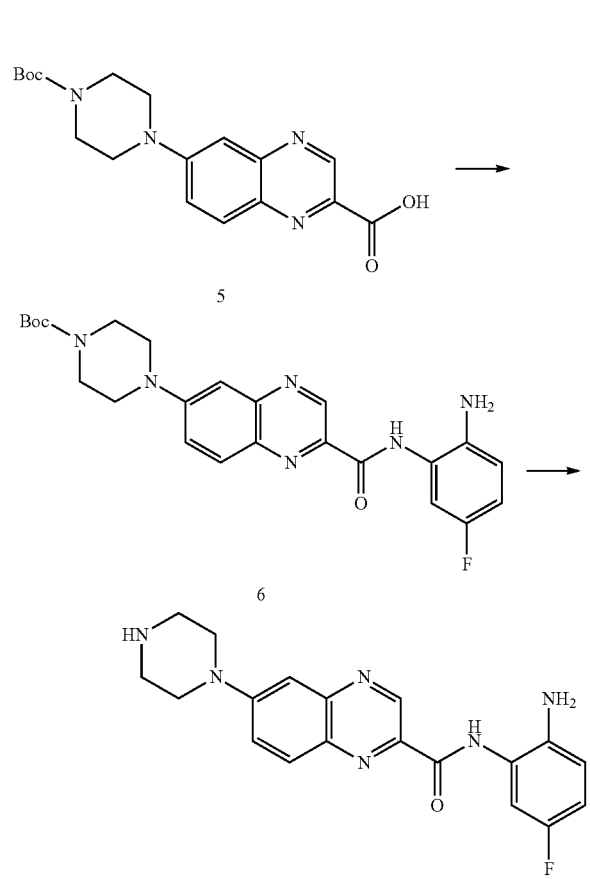 [SMILES: CC(C)(C)OC(=O)N1CCN(c2ccc3nc(C(=O)O)cnc3c2)CC1 ; CC(C)(C)OC(=O)N1CCN(c2ccc3nc(C(=O)Nc4cc(F)ccc4N)cnc3c2)CC1 ; Nc1ccc(F)cc1NC(=O)c1cnc2cc(N3CCNCC3)ccc2n1]

Step 1: To a mixture of 6-(4-(tert-butoxycarbonyl)piperazin-1-yl)quinoxaline-2-carboxylic acid (150 mg, 0.42 mmol), EDCI (130 mg, 0.84 mmol), HOAT (114 mg, 0.84 mmol), in DMF (5 mL) was added DIPEA (217 mg, 1.68 mmol) and amine (95 mg, 0.42 mmol). The reaction mixture was heated to 60° C. overnight. The reaction was quenched with water, then extracted with EA, dried by anhydrous Na$_2$SO$_4$, and concentrated in vacuo to afford tert-butyl 4-(2-(2-amino-5-fluorophenylcarbamoyl)quinoxalin-6-yl)piperazine-1-carboxylate as a yellow solid (60 mg, yield: 25%).

Step 2: To a solution of tert-butyl 4-(2-(2-amino-5-fluorophenylcarbamoyl)quinoxalin-6-yl)piperazine-1-carboxylate (60 mg, 0.1 mmol) in 5 ml CH2Cl2 was added 0.2 ml TFA, followed by stirring at r.t. for 2 hrs. The mixture was concentrated in vacuo. The residue was purified by Pre-HPLC to afford Compound O(10 mg, yield: 27%) as a yellow solid. $^1$H NMR (500 MHz, DMSO): δ 10.15 (s, 1H), 9.23 (s, 1H), 8.28 (s, 1H), 8.00 (d, J=9.5 Hz, 1H), 7.87 (d, J=6 Hz, 1H), 7.55 (d, J=11 Hz, 2H), 7.33 (s, J=2.5 Hz, 1H), 6.88 (m, 2H), 4.89 (br, 2H), 3.42 (s, 4H), 2.96 (s, 4H), LCMS: m/z=367 (M+H)$^+$.

Example 18

HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 μM tris(2-carboxyethyl)phosphine) to 6 fold their final concentration. The HDAC enzymes (purchased from BPS Biosciences) were diluted to 1.5 fold their final concentration in assay buffer and pre-incubated with the compounds for 24 hours prior to addition of the substrate.

The substrate tripeptide substrate 3 (synthesized in house) for each enzyme was equal to the Km as determined by a substrate titration curve. The enzyme and substrate concentrations used are given in Table 2. The substrates were diluted in assay buffer at 6× their final concentration with 0.3 μM sequencing grade trypsin (Sigma). The substrate/trypsin mix was added to the enzyme/compound mix, the plate was shaken for 60 seconds and placed into a Spectramax M5 microtiter plate reader. The development of fluorescence was monitored for 30 min. and the linear rate of the reaction was calculated. The $IC_{50}$ was determined using Graph Pad Prism by a four parameter curve fit. The $IC_{50}$ values obtained for the compounds of this invention are found in Table 1.

TABLE 2

| | Enzyme concentration | Substrate concentration |
|---|---|---|
| HDAC1 | 3.5 ng/μl | 3.8 μM |
| HDAC2 | 0.2 ng/μl | 2.3 μM |
| HDAC3 | 0.08 ng/μl | 3.9 μM |

Example 19

HDAC Inhibition Assays

Tissue culture media were first removed from T75 flasks containing confluent A549 and NCI-H520 lung cells. The flasks were then washed with PBS. 10 ml enzyme free cell dissociation media was added in to the flasks followed by 30-minute incubation at 37 C in 5% $CO_2$. The flasks were lightly tapped to ensure that any cells still adhering to the flask were dislodged before the media with cells were transferred to 50 ml tubes.

The media with cells were then spanned and aspirated before 10 ml complete growth media were added. Single cell suspensions were then created by repeat pipetting. Cells were counted and volume was adjusted to $10^5$ cells/ml. 5 μl of cells were added to 384 well plates pre-plated with 15 ul complete growth media. Testing compounds were dispensed at the indicated dose ranges. The plates were spanned for 10 seconds at 1000 rpm to settle the cells followed by 48 hour incubation at 37 C in 5% $CO_2$. 5 μl of MTS reagent were added to the plates followed by 1 hour incubation at 37 C in 5% $CO_2$.

Optical densities were read at 650 nm and 490 nm. Corrected OD values (OD490-OD650) were plotted as displayed. Cisplatin $IC_{50}$ values were calculated by Graphpad Prism software and plotted as displayed.

Incorporation by reference

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Equivalents

Those skilled in the art will recognize, or be able to ascertain using no more than routine experimentation, many equivalents of the specific embodiments of the invention described herein. Such equivalents are intended with be encompassed by the following claims.

We claim:
1. A method of treating cancer, a neurodegenerative disease, or a metabolic disease, in a subject comprising administering to the subject a compound selected from

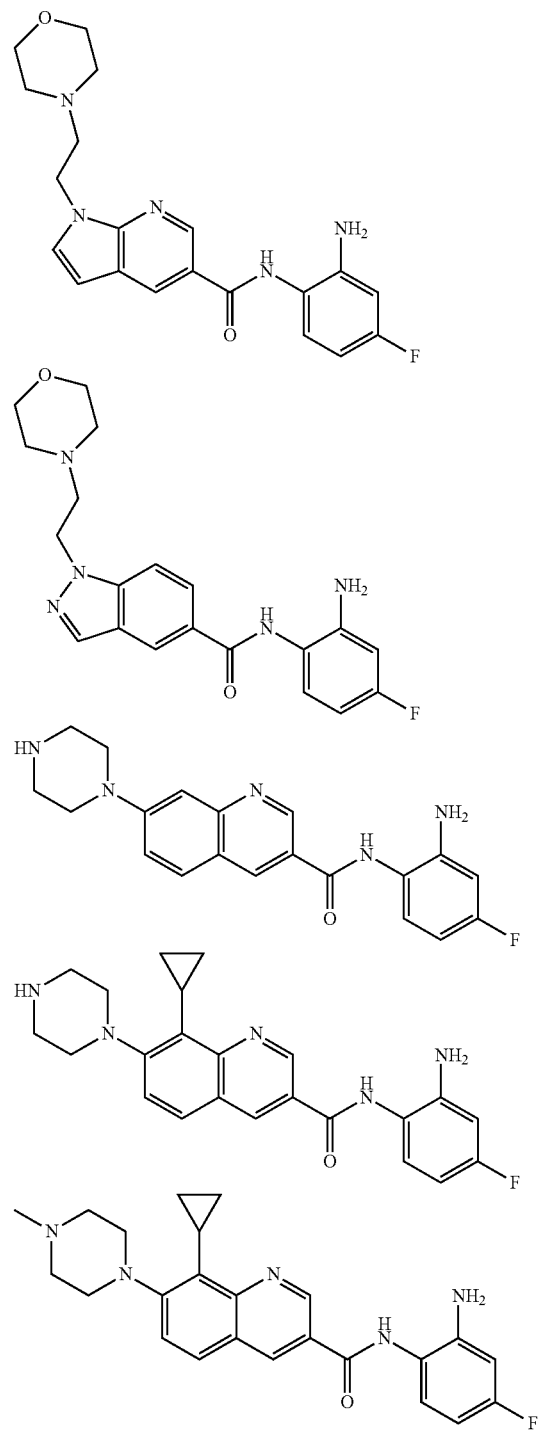

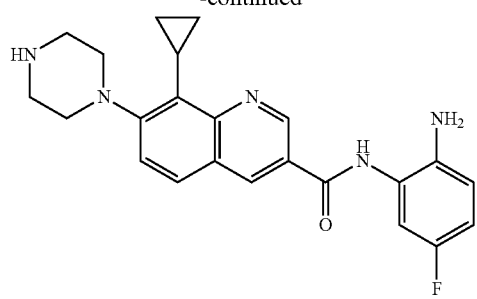
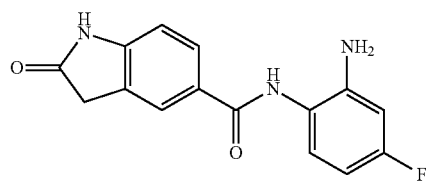
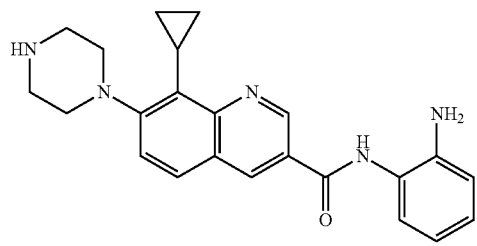
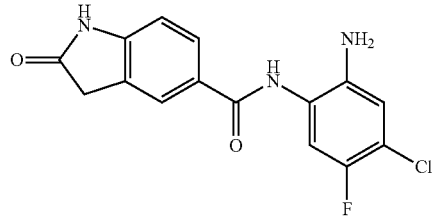
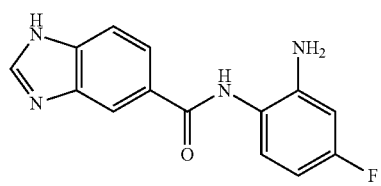
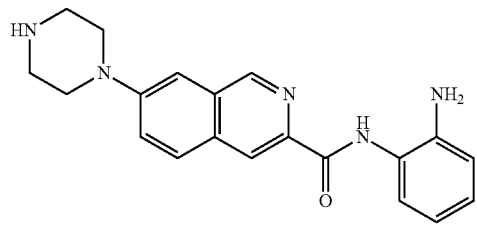
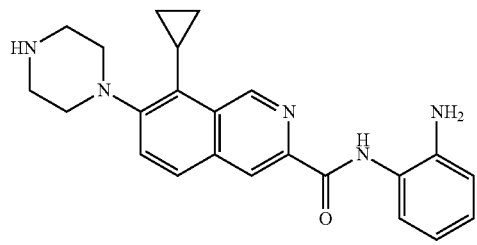
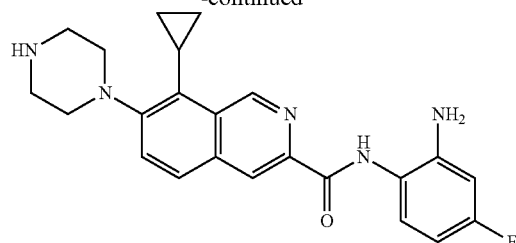
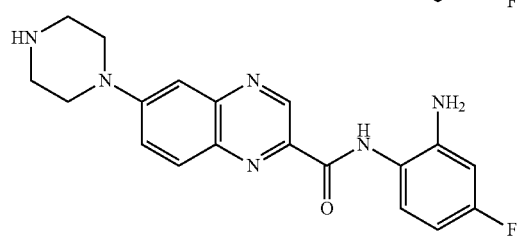
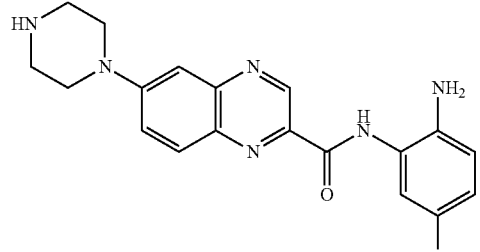
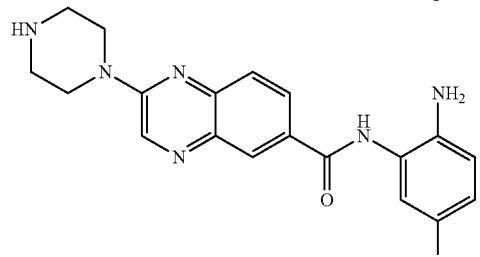
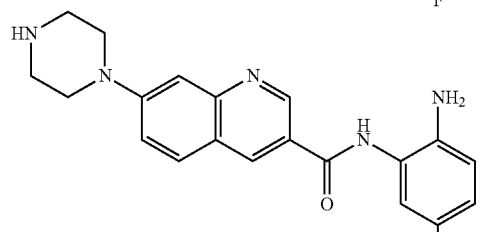
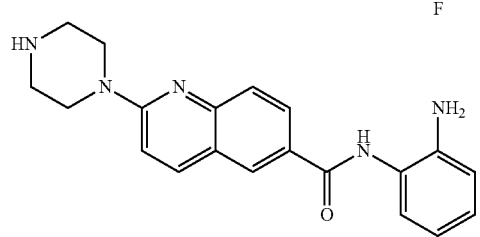
and pharmaceutically acceptable salts thereof.
2. The method of claim 1, wherein the cancer is a hematologic malignancy.
3. The method of claim 2, wherein the hematologic malignancy is a leukemia or lymphoma.

4. The method of claim 3, wherein the leukemia is acute lymphoblastic leukemia (ALL), acute myelogenous leukemia (AML), chronic lymphocytic leukemia (CLL), chronic myelogenous leukemia (CML), acute monocytic leukemia (AML), or acute promyelocytic leukemia (APL).

5. The method of claim 3, wherein the lymphoma is Hodgkin's lymphoma or Non-Hodgkin's lymphoma.

6. The method of claim 1, wherein the cancer is a solid tumor.

7. The method of claim 6, wherein the solid tumor is a brain tumor, neuroblastoma, retinoblastoma, Wilm's tumor, bone tumors, soft-tissue sarcomas, head cancer, neck cancer, gastric cancer, prostate cancer, bladder cancer, renal cancer, cancer of the uterus, ovarian cancer, testicular cancer, colon cancer, lung cancer, or breast cancer.

8. The method of claim 1, wherein the cancer is gastric cancer, prostate cancer, or colorectal cancer.

9. The method of claim 1, wherein the neurodegenerative disease is Huntington's disease, Friedrich's ataxia, myotonic dystrophy, Parkinson's disease, spinocerebellar ataxia, Kennedy's disease, amyotrophic lateral sclerosis, spinal and bulbar muscular atrophy, or Alzheimer's disease.

10. The method of claim 1, wherein the metabolic disease is type 2 diabetes.

11. The method of claim 1, wherein the subject is a human.

* * * * *